US011498912B2

(12) United States Patent
Conroy et al.

(10) Patent No.: US 11,498,912 B2
(45) Date of Patent: Nov. 15, 2022

(54) RADICAL COMPOUNDS AND METHODS OF USING THEREOF

(71) Applicant: Ohio State Innovation Foundation, Columbus, OH (US)

(72) Inventors: Daniel W. Conroy, Columbus, OH (US); Christopher P. Jaroniec, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/636,530

(22) PCT Filed: Aug. 6, 2018

(86) PCT No.: PCT/US2018/045429
§ 371 (c)(1),
(2) Date: Feb. 4, 2020

(87) PCT Pub. No.: WO2019/028473
PCT Pub. Date: Feb. 7, 2019

(65) Prior Publication Data
US 2021/0179581 A1 Jun. 17, 2021

Related U.S. Application Data

(60) Provisional application No. 62/541,334, filed on Aug. 4, 2017.

(51) Int. Cl.
| | | |
|---|---|---|
| *C07D 401/12* | (2006.01) | |
| *C07D 211/94* | (2006.01) | |
| *C07D 221/20* | (2006.01) | |
| *C07D 491/20* | (2006.01) | |
| *G01N 24/12* | (2006.01) | |
| *G01R 33/62* | (2006.01) | |

(52) U.S. Cl.
CPC .......... *C07D 401/12* (2013.01); *C07D 211/94* (2013.01); *C07D 221/20* (2013.01); *C07D 491/20* (2013.01); *G01N 24/12* (2013.01); *G01R 33/62* (2013.01)

(58) Field of Classification Search
CPC .. C07D 401/12; C07D 211/94; C07D 221/20; C07D 491/20
See application file for complete search history.

(56) References Cited

U.S. PATENT DOCUMENTS

| 6,311,086 B1 | 10/2001 | Delano |
| 2016/0046643 A1 | 2/2016 | Sauvee et al. |

OTHER PUBLICATIONS

Dulog; Advanced Materials 1992, 4(5), 349-351. DOI: 10.1002/adma.19920040506 (Year: 1992).*
Bui; J. Chem. Soc., Perkin Trans. 2, 2000, 1043-1046. doi: 10.1039/a909033i (Year: 2000).*
Gobbo; Journal of Peptide Science, 2012, 18, 37-44. doi: 10.1002/psc.1413 (Year: 2012).*
Hanson; J. Am. Chem. Soc. 1996, 118, 7618-7625. doi: 10.1021/ja961025u (Year: 1996).*
Crisma; Journal of Peptide Research 2005, 65, 564-579. doi: 10.1111/j.1399-3011.2005.00258.x (Year: 2005).*
Elsaesser; Magnetic Resonance in Chemistry 2005, 43(Spec.Issue), S26-S33. doi: 10.1002/mrc.1692 (Year: 2005).*
Hanson; Journal of the American Chemical Society 1996, 118, 271-272. doi: 10.1021/JA952423K (Year: 1996).*
Hanson; Molecular Physics 1998, 95, 957-966. doi: 10.1080/00268979809483229 (Year: 1998).*
Martin; Journal of Peptide Research 2001, 58, 424-432. doi: 10.1034/j.1399-3011.2001.00940.x (Year: 2001).*
McNulty; Biopolymers 2000, 55, 479-85. DOI: 10.1002/1097-0282(2000)55:6<479::AID-BIP1023>3.0.CO;2-F (Year: 2000).*
Sartori; Chem Phys Chem 2005, 6, 1472-1475. doi: 10.1002/cphc.200500139 (Year: 2005).*
Schreier; Biophys Rev 2012, 4, 45-66. DOI: 10.1007/s12551-011-0064-5 (Year: 2012).*
Smythe; Journal of the American Chemical Society 1995, 117, 10555-10562. doi: 10.1021/ja00147a018 (Year: 1995).*
Dulog; Liebigs Ann. Chem. 1992, 4, 301-303. https://doi.org/10.1002/jlac.199219920155 (Year: 1992).*
International Search Report and Written Opinion issued by the International Searching Authority (ISA/US) in PCT Application No. PCT/US2018/045429 dated Oct. 24, 2018. 9 pages.
McNulty, Joseph C., et al. "Electron spin resonance of TOAC labeled peptides: folding transitions and high frequency spectroscopy." Peptide Science 55.6 (2000): 479-485.
Toniolo, Claudio, et al. "Synthesis and conformational studies of peptides containing TOAC, a spin-labelled Cα, α-disubstituted glycine." Journal of peptide science: an official publication of the European Peptide Society 1.1 (1995): 45-57.

(Continued)

*Primary Examiner* — Daniel R Carcanague
(74) *Attorney, Agent, or Firm* — Meunier Carlin & Curfman LLC

(57) ABSTRACT

Disclosed are methods for performing dynamic nuclear polarization using the polarizing agents described herein. In general, the methods involve (a) providing a frozen sample in a magnetic field, wherein the frozen sample includes a polarizing agent described herein and an analyte with at least one spin half nucleus; (b) polarizing the at least one spin half nucleus of the analyte by irradiating the frozen sample with radiation having a frequency that excites electron spin transitions in the polarizing agent; (c) optionally melting the sample to produce a molten sample; and (d) detecting nuclear spin transitions in the at least one spin half nucleus of the analyte in the frozen or molten sample. In certain embodiments, the polarizing agents can be peptide-based. In these embodiments, the polarizing agents can be readily prepared by solid-phase peptide synthesis.

23 Claims, 15 Drawing Sheets

(56) References Cited

OTHER PUBLICATIONS

Jagtap, Anil P., et al. "bcTol: a highly water-soluble biradical for efficient dynamic nuclear polarization of biomolecules." Chemical Communications 52.43 (2016): 7020-7023.
International Preliminary Report on Patentability issued in PCT/US2018/045429, dated Feb. 13, 2020.

* cited by examiner

RADICAL COMPOUNDS AND METHODS OF USING THEREOF

CROSS-REFERENCE TO RELATED APPLICATIONS

This application is a national stage application filed under 35 U.S.C. § 371 of PCT/US2018/045429 filed Aug. 6, 2018, which claims benefit of U.S. Provisional Application No. 62/541,334 filed Aug. 4, 2017, which is hereby incorporated herein by reference in its entirety.

STATEMENT REGARDING FEDERALLY SPONSORED RESEARCH OR DEVELOPMENT

This invention was made with government support under MCB1243461 awarded by the National Science Foundation. The government has certain rights in the invention.

BACKGROUND

There is an interest in preparing samples with high nuclear spin polarizations with the goal of increasing signal intensities in nuclear magnetic resonance (NMR) spectra and magnetic resonance imaging (MSI) images. Example approaches include high frequency, microwave driven dynamic nuclear polarization (DNP), para hydrogen induced polarization (PHIP), polarization of noble gases (e.g., He, Xe and, Kr), and optically pumped nuclear polarization of semiconductors and photosynthetic reaction centers and other proteins. Dynamic nuclear polarization is an approach in which the large spin polarization in an electron spin system is transferred to a nuclear spin reservoir via microwave irradiation of the electron paramagnetic resonance (EPR) spectrum. The electron spin system in DNP is provided by an endogenous or exogenous paramagnetic polarizing agent. A number of polarizing agents have been investigated, including monoradicals (e.g., TEMPO-based radicals, trityl radicals, etc.) and biradicals (e.g., bis-TEMPO-2-ethyleneglycol (BT2E), where TEMPO is 2,2,6,6-tetramethylpiperidin-1-oxyl and n=2 indicates a tether of two ethylene gly col units). While some polarizing agents are known, there remains a need in the art for improved polarizing agents and in particular improved biradical polarizing agents.

SUMMARY

Disclosed herein are compounds defined by Formula I below

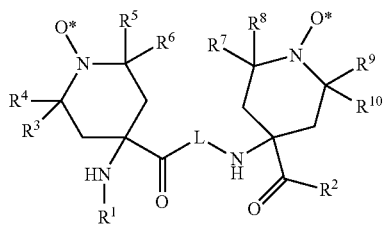

Formula I wherein L represents a direct bond or a linking group; $R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$cycloalkyl-$C_{1-4}$alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups; $R^2$ is selected from the group consisting of hydrogen, hydroxy, $-OR^{11}$, $C_{1-6}$ alkyl, $C_{2-6}$ alkenyl, $C_{2-6}$ alkynyl, $C_{3-10}$ cycloalkyl, 6-membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups; $R^3$ and $R^4$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^3$ and $R^4$, together with the carbon atom to which they are attached, form a 3-10 membered cycloalkyl or 4-10 membered heterocycloalkyl ring each optionally substituted with 1, 2, 3, or 4 independently selected $R^X$ groups; $R^5$ and $R^6$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^5$ and $R^6$, together with the carbon atom to which they are attached, form a 3-10 membered cycloalkyl or 4-10 membered heterocycloalkyl ring each optionally substituted with 1, 2, 3, or 4 independently selected $R^X$ groups; $R^7$ and $R^8$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^7$ and $R^8$, together with the carbon atom to which they are attached, form a 3-10 membered cycloalkyl or 4-10 membered heterocycloalkyl ring each optionally substituted with 1, 2, 3, or 4 independently selected $R^X$ groups; $R^9$ and $R^{10}$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^9$ and $R^{10}$, together with the carbon atom to which they are attached, form a 3-10 membered cycloalkyl or 4-10 membered heterocycloalkyl ring each optionally substituted with 1, 2, 3, or 4 independently selected $R^X$ groups; $R^u$ is selected from the group consisting of $C_{1-6}$ alkyl, $C_{2-6}$ alkenyl, $C_{2-6}$ alkynyl, $C_{3-10}$ cycloalkyl, 6-10 membered and, 5-10 membered heteroaryl, 4-10 membered heterocycloalkyl, $C_{3-10}$ cycloalkyl-$C_{1-4}$ alkyl ene, 4-10 membered heterocycloalkyl-$C_{1-4}$alkylene, 6-10 membered aryl-$C_{1-4}$ alkylene, 5-10 membered heteroaryl-$C_{1-4}$alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkyl aminosulfonyl amino, di($C_{1-6}$ alkyl)aminosulfonyl amino, aminocarbonylamino, $C_{1-6}$ alkylaminocarbonylamino, and di($C_{1-6}$ alkyl)aminocarbonylamino.

The compounds described herein can be used as polarizing agents for performing dynamic nuclear polarization. Accordingly, also provided are methods that comprise (a) providing a frozen sample in a magnetic field, wherein the frozen sample includes a polarizing agent described herein and an analyte with at least one spin half nucleus; (b) polarizing the at least one spin half nucleus of the analyte by irradiating the frozen sample with radiation having a frequency that excites electron spin transitions in the polarizing agent; (c) optionally melting the sample to produce a molten sample; and (d) detecting nuclear spin transitions in the at least one spin half nucleus of the analyte in the frozen or molten sample. In certain embodiments, the methods further comprise a step of freezing a sample in a magnetic field to provide the frozen sample in a magnetic field. In one such embodiment, the sample is melted prior to detection and the freezing, polarizing, melting and detecting steps are repeated at least once.

DETAILED DESCRIPTION

Definitions

Figure 1:
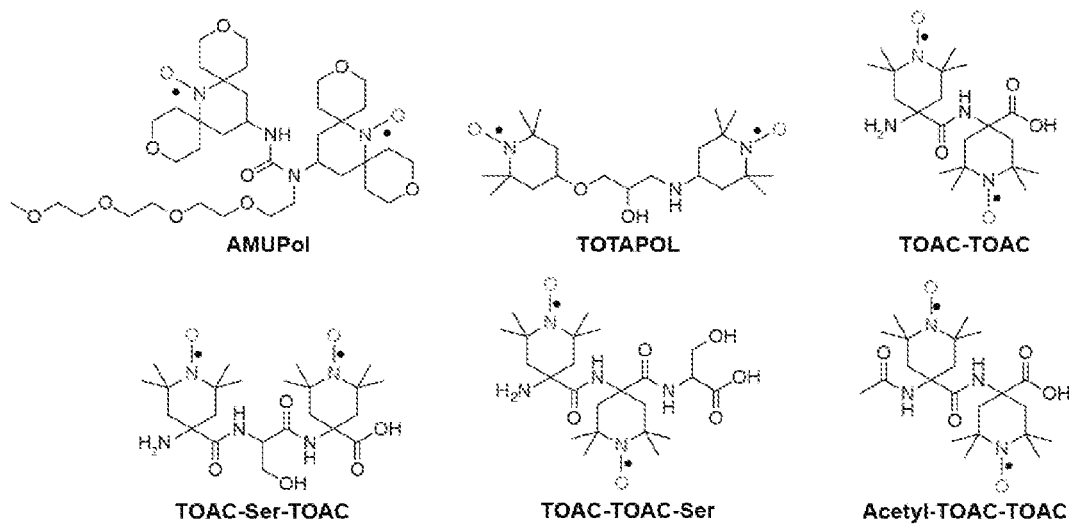
FIG. 1 shows the structures of nitroxide biradicals: AMUPOL, TOTAPOL, TOAC-TOAC (TT), TOAC-Ser-TOAC (TST), TOAC-TOAC-Ser (TTS) & acetyl-TOAC-TOAC (ATT).
Figure 2A:
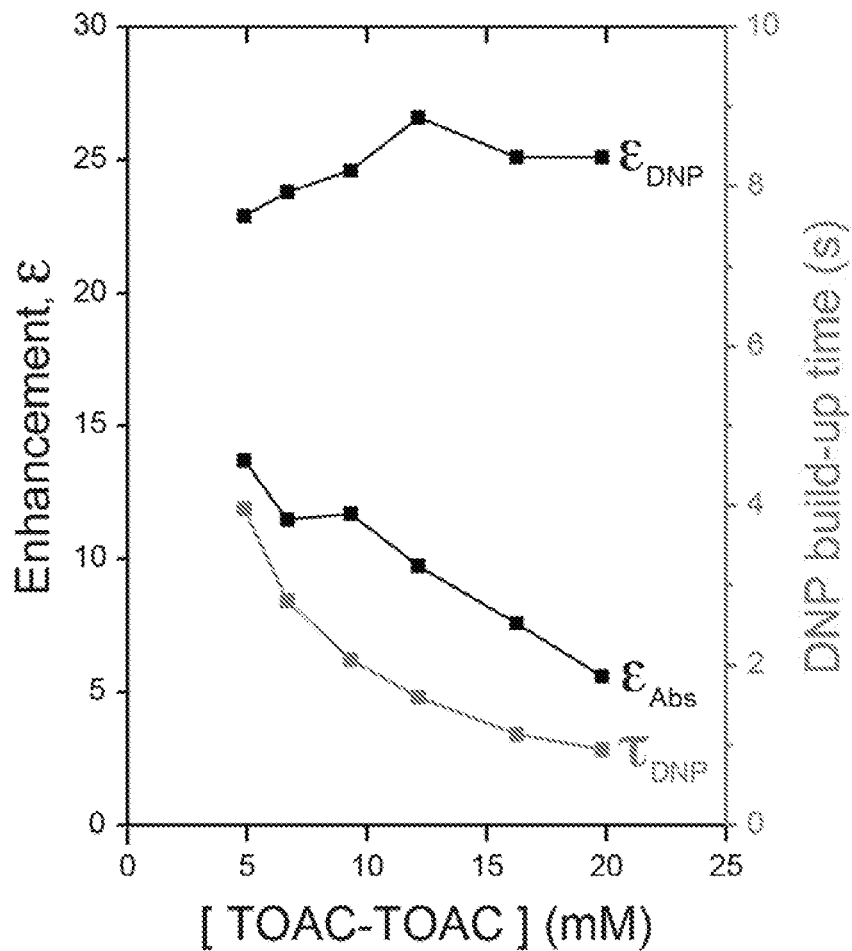
FIG. 2A shows the DNP enhancement profiles of TT as a function of concentration: microwaves on/off signal enhancement, εDNP, and the absolute signal enhancement between doped and undoped samples, εAbs. The DNP build-up time, τDNP, as a function of biradical concentration, is also shown.
Figure 2B:
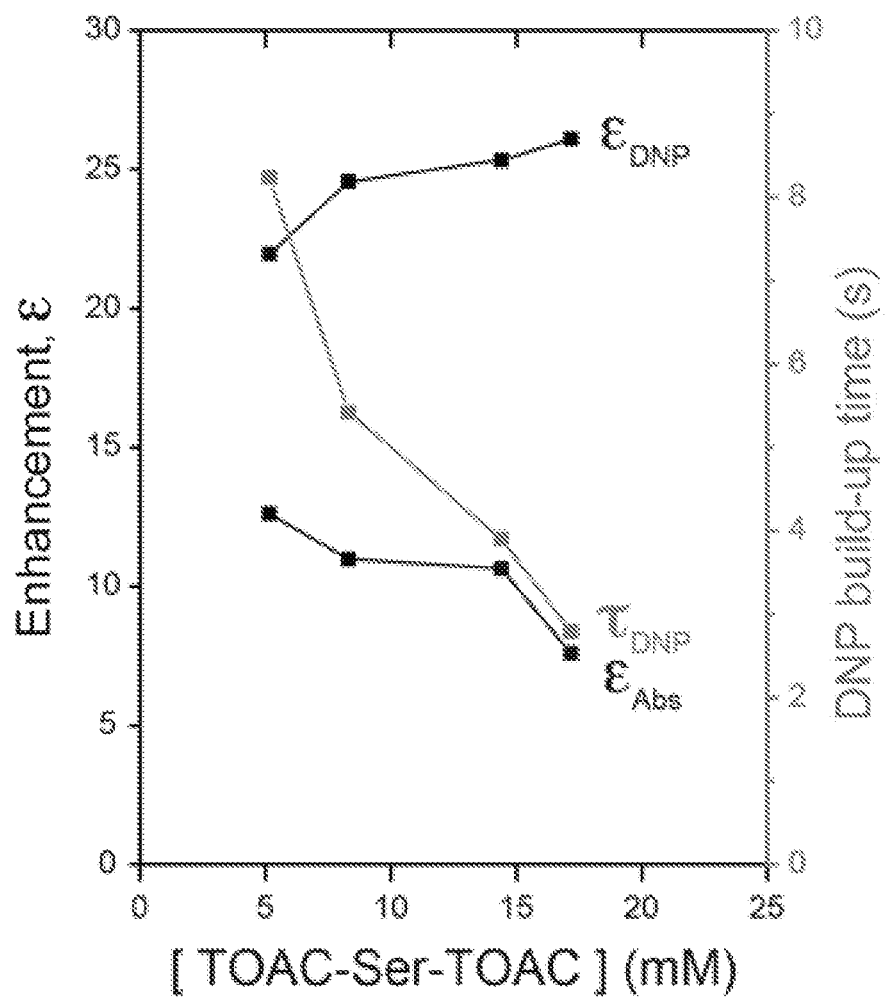
FIG. 2B shows the DNP enhancement profiles of TST as a function of concentration: microwaves on/off signal enhancement, εDNP, and the absolute signal enhancement between doped and undoped samples, εAbs. The DNP build-up time, τDNP, as a function of biradical concentration, is also shown.
Figure 2C:
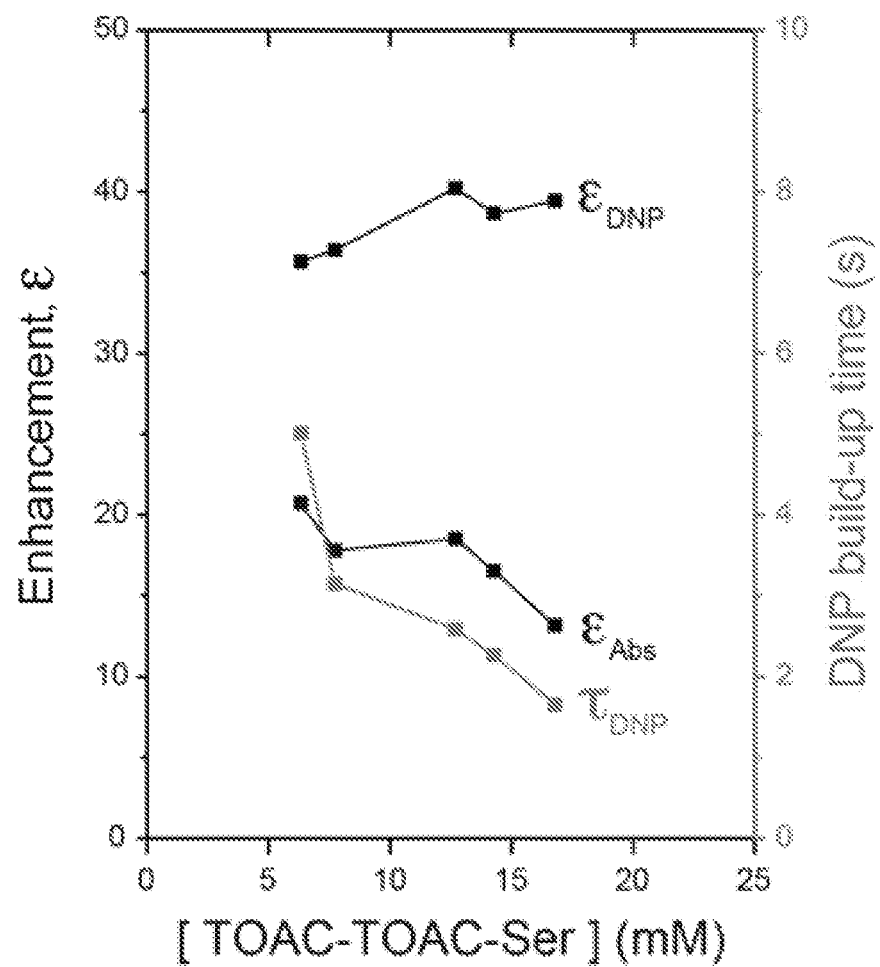
FIG. 2C shows the DNP enhancement profiles of TTS as a function of concentration: microwaves on/off signal enhancement, εDNP, and the absolute signal enhancement between doped and undoped samples, εAbs. The DNP build-up time, τDNP, as a function of biradical concentration, is also shown.
Figure 2D:
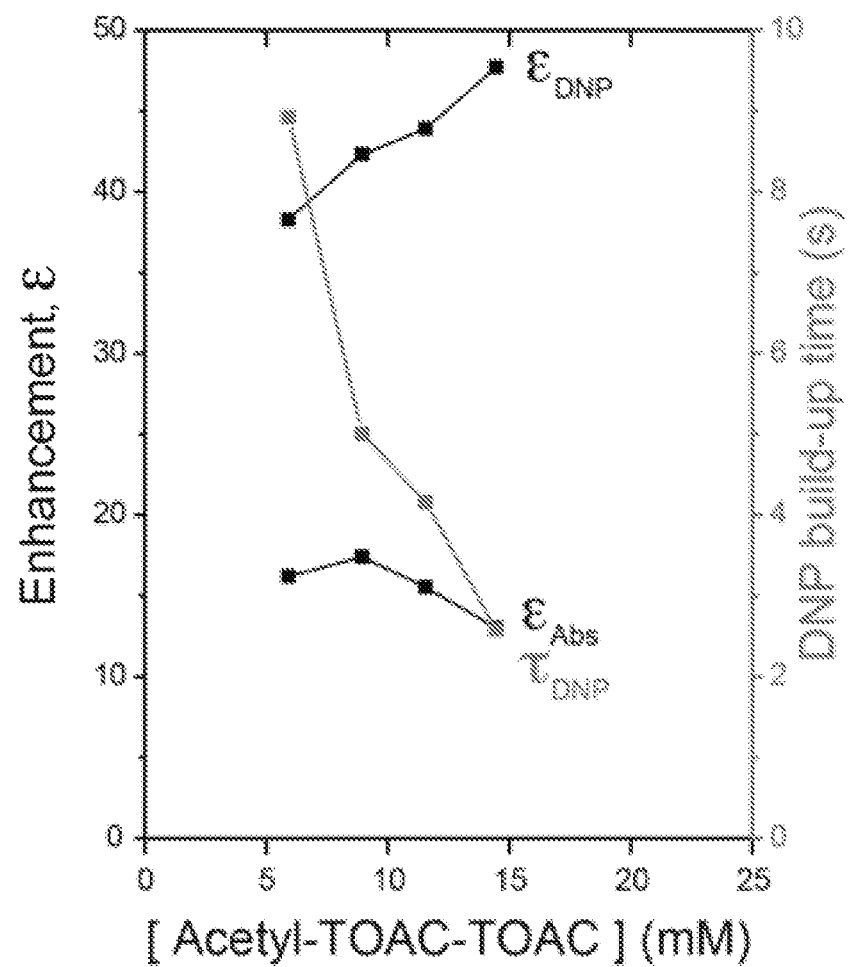
FIG. 2D shows the DNP enhancement profiles of ATT as a function of concentration: microwaves on/off signal enhancement, εDNP, and the absolute signal enhancement between doped and undoped samples, εAbs. The DNP build-up time, τDNP, as a function of biradical concentration, is also shown.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxy carbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(O)— group, which may also be written as C(O).

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N. O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

"Linker," "Linking Moiety," or "Linking Group", as used herein, refer to a bivalent group or moiety which connects the two radical moieties in the compounds described herein. The linker can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, more preferably between 3 and 50 atoms, most preferably between 3 and 20 atoms. The linker can serve to modify the solubility of the compounds described herein. In some embodiments, the linker is hydrophilic. In some embodiments, the linker is hydrophobic. In some embodiments, the linker can be an alkyl group, an alkyl aryl group, an oligo- or polyalkylene oxide chain (e.g., an oligo- or polyethylene glycol chain), or an oligo- or poly(amino acid) chain.

The term "amino acid," as used herein, refers to both natural and non-natural amino acids, and analogs and derivatives thereof. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the common naturally occurring amino acids or the rare natural amino acids selenocysteine or pyrolysine. Examples of suitable amino acids include, but are not limited to, alanine, alloisoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These are listed in the table 1 along with their abbreviations used herein.

| Amino Acid | Abbreviations* L-amino acid | Abbreviations* D-amino acid |
| --- | --- | --- |
| Alanine | Ala (A) | ala (a) |
| Allosoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| Glutamine | Gln (Q) | gln (q) |
| Glycine | Gly (G) | gly (g) |
| Histidine | His (H) | his (h) |
| Homoproline (aka pipecolic acid) | Pip (Θ) | pip (θ) |
| Isoleucine | Ile (I) | ile (i) |
| Leucine | Leu (L) | leu (l) |
| Lysine | Lys (K) | lys (k) |
| methionine | Met (M) | met (m) |
| napthylalanine | Nal (Φ) | nal (Φ) |
| norleucine | Nle (Ω) | nle |
| phenylalanine | Phe (F) | phe (F) |
| phenylglycine | Phg (Ψ) | phg |
| 4-(phosphonodifluoromethyl)phenyl-alanine | F$_2$Pmp (Λ) | f$_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| 2,2,6,6-tetramethyl-N-oxyl-4-amino-4-carboxylic acid | TOAC (TOAC) | toac (toac) |
| Valine | Val (V) | val (v) |
| 2,3-diaminopropionic acid | Dap | dap |

*single letter abbreviations: when shown in capital letters herein it indicates the L-amino acid form, when shown in lower case herein it indicates the D-amino acid form As discussed above, non-natural amino acids and D-amino acids can be used herein. In some cases, amino acids can be coupled by a peptide bond. Each amino acid can be coupled to an adjacent amino acid at the amino group, the carboxylate group, or the side chain.

The term "poly(amino acid)," as used herein, refers to a moiety comprising a plurality of amino acids coupled by peptide bonds. Poly(amino acid) groups can comprise from 2 to 500. from 2 to 250, from 2 to 100, from 2 to 50, from 2 to 25, from 2 to 20, from 2 to 15, from 2 to 10, from 2 to 5, from 2 to 4, or from 2 to 3 amino acid residues. In some embodiments, the poly(amino acid) group can be a dipeptide. In some embodiments, the poly(amino acid) group can be a tripeptide. In some embodiments, the poly(amino acid) group can be a tetrapeptide. In some embodiments, the poly(amino acid) group can comprise a protein. In certain embodiments, the protein can be an analyte of interest.

The term "direct bond" or "bond" refers to a single, double or triple bond between two groups. In certain embodiments, a "direct bond" refers to a single bond between two groups The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-inline pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (KL)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p, 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and aryl amines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride, and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Compounds

The sensitivity in solid-state NMR (ssNMR) experiments can be enhanced by two to three orders of magnitude by dynamically polarizing the nuclear spin system prior to recording the NMR spectrum. This enhancement can be transferred into the liquid-state (e.g., liquid-state NMR or MRI) by melting the solid sample after polarization. For MRI applications, at least a portion of the molten sample that includes a polarized analyte is administered into the subject being imaged prior to imaging.

The DNP procedure involves microwave irradiation of the electron paramagnetic resonance (EPR) spectrum of either an endogenous or exogenous paramagnetic species present in a sample, and results in the transfer of the greater spin polarization of the electrons to the nuclei of surrounding molecules. While the methods described herein are not limited to any specific magnetic field and the DNP procedure could be performed at low magnetic fields, the performance of dynamic nuclear polarization (DNP) experiments at the high magnetic fields used in contemporary NMR experiments (e.g., 5-20 T) is affected by the following three factors.

First, a high frequency (140-600 GHz), high power (~10 watts) microwave source is typically used to drive the continuous-wave (CW) DNP transitions associated with the second order electron-nuclear dipolar interactions (though other sources, such as pulsed and chirped microwave irradiation can also be used). To date this has been achieved by utilizing gyrotrons since they operate in the requisite frequency range and produce suitable microwave powers.

Second, the relaxation times of the spin systems in the experiment dictate that it be optimally performed at low temperatures (usually ≤90 K). When obtaining high resolution ssNMR spectra of solids, magic-angle spinning (MAS) is preferably incorporated into the experiment. Thus, multiple resonance—i.e., $^1H$, $^{13}C$, $^{15}N$ and $e^-$—low temperature MAS probes may be required for optimal execution of certain DNP experiments.

The third factor is the nature of the paramagnetic polarizing agent. Preferably, the polarizing agent should: (a) be compatible with the polarization mechanism that yields the optimal signal enhancement, namely the three-spin thermal mixing (TM) or cross effect (CE), (b) be useful in polarizing a large array of analytes ranging from small molecules to proteins, (c) produce large signal enhancements at a reduced concentration of paramagnetic species, and (d) be soluble in aqueous media.

The compounds described herein can satisfy one or more of the criteria above. In some embodiments, the compounds described herein can satisfy at least the first three criteria. In certain embodiments, can satisfy the first three criteria as well as the fourth requirement (i.e., solubility in aqueous media).

Provided herein are compounds defined by Formula I below

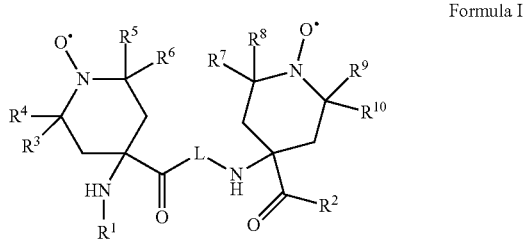

Formula I wherein L represents a direct bond or a linking group; $R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkyl carbonyl, $C_{1-12}$ alkoxy carbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups; $R^2$ is selected from the group consisting of hydrogen, hydroxy, $-OR^{11}$, $C_{1-6}$ alkyl, $C_{2-6}$ alkenyl, $C_{2-6}$ alkynyl, $C_{3-10}$ cycloalkyl, 6-membered aryl, 5-10 membered heteroaryl, 4-10 membered heterocycloalkyl, $C_{3-10}$ cycloalkyl-$C_{1-4}$alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$alkylamino; di($C_{1-12}$-alkyl)amino, amino acid, poly(amino acid), and poly(alkylene oxide), each optionally substituted with 1, 2, 3, or 4 independently selected $R^X$ groups; $R^3$ and $R^4$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^3$ and $R^4$, together with the carbon atom to which they are attached, form a 3-10 membered cycloalkyl or 4-10 membered heterocycloalkyl ring each optionally substituted with 1, 2, 3, or 4 independently selected $R^X$ groups; $R^5$ and $R^6$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^5$ and $R^6$, together with the carbon atom to which they are attached, form a 3-10 membered cycloalkyl or 4-10 membered heterocycloalkyl ring each optionally substituted with 1, 2, 3, or 4 independently selected $R^X$ groups; $R^7$ and $R^8$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^7$ and $R^8$, together with the carbon atom to which they are attached, form a 3-10 membered cycloalkyl or 4-10 membered heterocycloalkyl ring each optionally substituted with 1, 2, 3, or 4 independently selected $R^X$ groups; $R^9$ and $R^{50}$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^9$ and $R^{10}$, together with the carbon atom to which they are attached, form a 3-10 membered cycloalkyl or 4-10 membered heterocycloalkyl ring each optionally substituted with 1, 2, 3, or 4 independently selected $R^X$ groups; $R^u$ is selected from the group consisting of $C_{1-6}$ alkyl, $C_{2-6}$ alkenyl, $C_{2-6}$ alkynyl, $C_{3-10}$cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)

carbamyl, carboxy, $C_{1-6}$ alkyl carbonyl, $C_{1-6}$ alkoxy carbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^3$, $R^4$, $R^5$, $R^9$, $R^7$, $R^8$, $R^9$, and $R^{10}$ are each $C_{1-6}$ alkyl ($C_{1-4}$ alkyl).

In certain embodiments, $R^3$, $R^4$, $R^5$, $R^6$, $R^7$, $R^8$, $R^9$, and $R^{10}$ are each ethyl.

In certain embodiments, $R^3$, $R^4$, $R^5$, $R^6$, $R^7$, $R^8$, $R^9$, and $R^{10}$ are each methyl. In these embodiments, the compound is defined by Formula IA

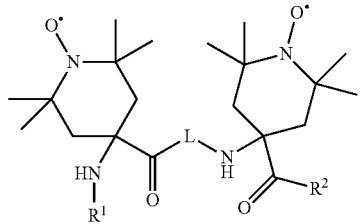

Formula IA wherein L represents a direct bond or a linking group; $R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxy carbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups; $R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-membered and, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups; $R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkyl carbonyl, $C_{1-6}$ alkoxy carbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In other embodiments, the compound can be defined by Formula IB

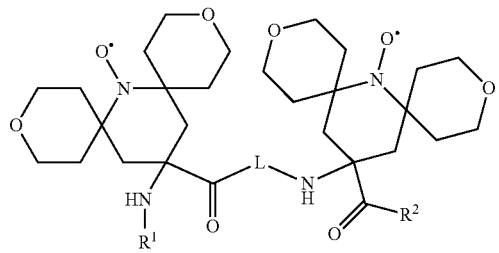

Formula IB wherein L represents a direct bond or a linking group; $R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkyl ene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups; $R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups; $R^u$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonyl amino, $C_{1-6}$ alkyl aminosulfonyl amino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In other embodiments, the compound is defined by Formula IC

Formula IC

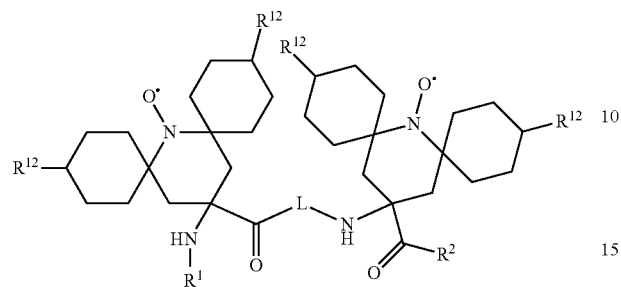

wherein L represents a direct bond or a linking group; $R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups; $R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups; $R^{11}$ is selected from the group consisting of $C_{1-6}$ alkyl, $C_{2-6}$ alkenyl, $C_{2-6}$ alkynyl, $C_{3-10}$cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; $R^{12}$ is selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$alkoxy, $C_{1-6}$ haloalkoxy, cyano-$C_{1-3}$ alkyl, HO—$C_{1-3}$ alkyl, amino, $C_{1-6}$alkylamino, di($C_{1-6}$alkyl)amino, thio, $C_{1-6}$alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkylaminosulfonylamino, aminocarbonylamino, $C_{1-6}$ alkylaminocarbonylamino, di($C_{1-6}$ alkylaminocarbonylamino, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$alkylene, 6-10 membered aryl $C_{1-4}$ alkylene, 5-10 membered heteroaryl-$C_{1-4}$ alkylene, and poly(alkylene oxide); and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$haloalkoxy, cyano-$C_{5-3}$ alkyl, HQ-CIG alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkylaminosulfonylamino, aminocarbonylamino, $C_{1-6}$ alkylaminocarbonylamino, and di($C_{1-6}$ alkyl)aminocarbonylamino.

In some embodiments, L represents a direct bond. For example, the compounds of Formula I can be represented by the formula below.

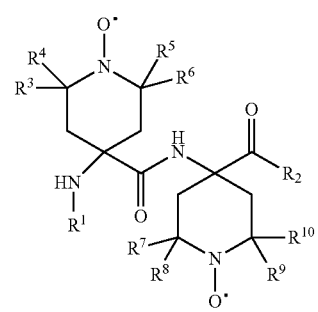

In other embodiments, L represents a linking group. In some embodiments, the linking group can comprise one or more amino acid residues. In certain embodiments, the linking group can consist of one or more amino acid residues (i.e., the compound can be a peptide-based biradical). For example, L can be defined by the structure below

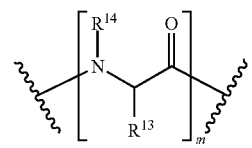

wherein for each occurrence in L, $R^{14}$ is H and $R^{13}$ is selected from one of the following

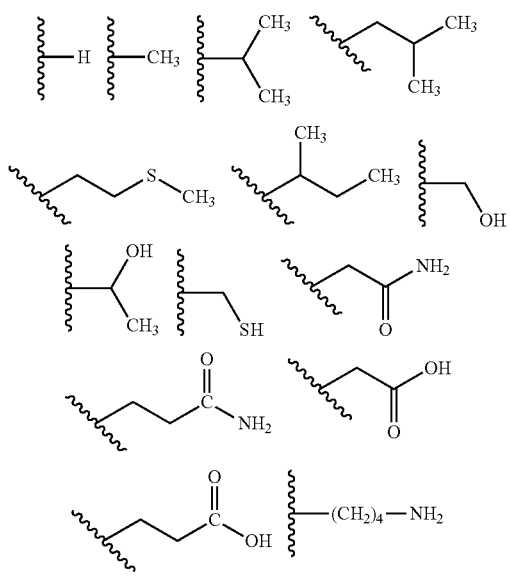

-continued

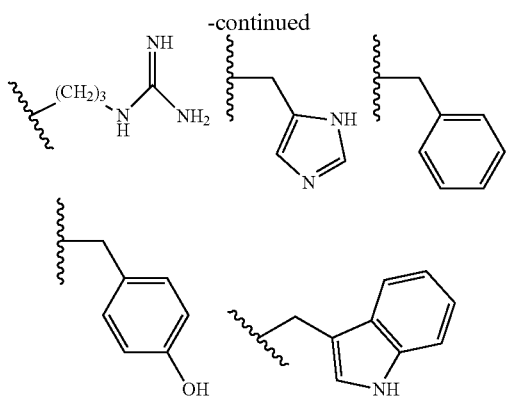

or $R^{13}$ and $R^{14}$, together with the atoms to which they are attached, form a five-membered heterocycle defined by the structure below

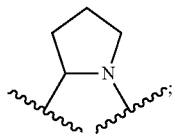

and
m is an integer selected from 1, 2, 3, 4, 5, and 6. In certain embodiments, m is 1. In other embodiments, m is 2. In some of these embodiments, L can comprise one or more amino acid residues selected from the group consisting of a serine residue, a threonine residue, an asparagine residue, a glutamine residue, an aspartic acid residue, a cysteine residue, a glutamic acid residue, and any combination thereof.

In some embodiments, L can comprise one or more unnatural amino acids. For example, L can comprise one or more 2,2,6,6-tetramethyl-N-oxyl-4-amino-4-carboxylic acid (TOAC) residues. In these embodiments, the compound can comprise, for example, three, four, five, six, seven eight, or more radicals.

In some embodiments, $R^1$ can comprise hydrogen. In other embodiments, $R^1$ can comprise a $C_{1-12}$ alkylcarbonyl or $C_{1-12}$ alkoxycarbonyl group. For example, $R^1$ can comprise an acetyl group. In some embodiments, $R^2$ comprises an amino acid residue. In certain embodiments, the amino acid residue is selected from the group consisting of a serine residue, a threonine residue, an asparagine residue, a glutamine residue, an aspartic acid residue, and a glutamic acid residue. In some embodiments, $R^1$ comprises a cysteine residue. In these cases, the cysteine residue can be used to covalently attach the polarizing agent to an analyte (e.g., a protein by way of a disulfide bond). In some embodiments, $R^1$ can comprise one or more unnatural amino acids. For example, $R^1$ can comprise one or more 2,2,6,6-tetramethyl-N-oxyl-4-amino-4-carboxylic acid (TOAC) residues. In these embodiments, the compound can comprise, for example, three, four, five, six, seven eight, or more radicals. In some embodiments, $R^1$ can comprise a poly(amino acid) sequence. The poly(amino acid) sequence can, for example, serves as a biomolecular recognition motif for an analyte of interest.

In some embodiments, $R^2$ can comprise a hydroxy group. In other embodiments, $R^2$ can comprise $OR^{11}$, where $R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups. In certain embodiments, $R^2$ can comprise $OR^{11}$ where $R^{11}$ is a $C_{1-6}$ alkyl group optionally substituted with 1, 2, 3, or 4 independently selected $R^X$ groups. In certain embodiments, $R^2$ can comprise $OR^{11}$ where $R^{11}$ is a $C_{1-6}$ a poly(alkylene oxide) group.

In some embodiments, $R^2$ comprises an amino acid residue. In certain embodiments, the amino acid residue is selected from the group consisting of a serine residue, a threonine residue, an asparagine residue, a glutamine residue, an aspartic acid residue, and a glutamic acid residue. In some embodiments, $R^2$ comprises a cysteine residue. In these cases, the cysteine residue can be used to covalently attach the polarizing agent to an analyte (e.g., a protein by way of a disulfide bond). In some embodiments, $R^2$ can comprise one or more unnatural amino acids. For example, $R^2$ can comprise one or more 2,2,6,6-tetramethyl-N-oxyl-4-amino-4-carboxylic acid (TOAC) residues. In these embodiments, the compound can comprise, for example, three, four, five, six, seven eight, or more radicals. In some embodiments, $R^2$ can comprise a poly(amino acid) sequence. The poly(amino acid) sequence can, for example, serves as a biomolecular recognition motif for an analyte of interest.

In certain embodiments, the compound can be one of the following:

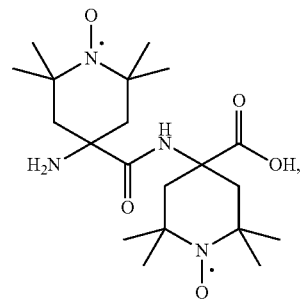
TOAC-TOAC

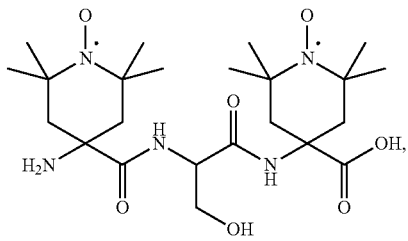
TOAC-Ser-TOAC

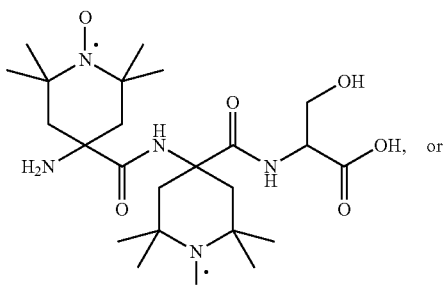
TOAC-TOAC-Ser

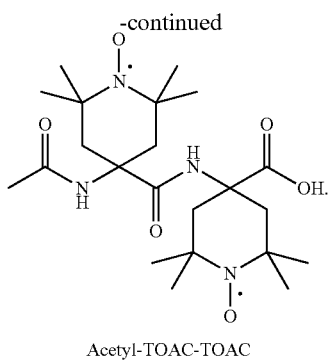

Acetyl-TOAC-TOAC

In some embodiments, the compounds described herein can be deuterated at one or more positions. For example, in some embodiments of Formula I, one or more of $R^3$, $R^4$, $R^5$, $R^6$, $R^7$, $R^8$, $R^9$, and $R^{10}$ can be deuterated (e.g., $R^3$, $R^4$, $R^5$, $R^6$, $R^7$, $R^8$, $R^9$, and $R^{10}$ can all be —$CD_3$). In other embodiments, deuterated moieties can be incorporated at $R^1$, $R^2$, L, or at other positions (e.g., at the meta positions of the TEMPO ring).

Methods of Use

In general, the methods involve (a) providing a frozen sample in a magnetic field, wherein the frozen sample includes a polarizing agent and an analyte with at least one spin half nucleus; (b) polarizing the at least one spin half nucleus of the analyte by irradiating the frozen sample with radiation having a frequency that excites electron spin transitions in the polarizing agent; (c) optionally melting the sample to produce a molten sample; and (d) detecting nuclear spin transitions in the at least one spin half nucleus of the analyte in the frozen or molten sample. The polarizing agent can be a compound (e.g., a biradical) described herein. In certain embodiments, the methods further comprise a step of freezing a sample in a magnetic field to provide the frozen sample in a magnetic field. In one such embodiment, the sample is melted prior to detection and the freezing, polarizing, melting and detecting steps are repeated at least once.

In certain embodiments, the analyte is a molecule (e.g., a protein) that is being studied by solid- or liquid-state NMR. In other embodiments, the analyte is an imaging agent that is being used for MRI. In such embodiments, the step of detecting is performed after at least a portion of the molten sample which comprises the polarized imaging agent has been administered to the subject being imaged. In general, the frozen sample may include any solvent; however, in certain embodiments, the frozen sample includes an amount of water, e.g., at least 50%, 60%, 70%, 80%, 90%, 95%, 99% or 100% by volume of water.

In one embodiment, the methods do not include a step of melting the sample to produce a molten sample. According to such embodiments, the sample is frozen in the detection step and the nuclear spin transitions in the at least one spin half nucleus of the analyte in the frozen sample are detected by solid-state NMR.

In another embodiment, the methods do include a step of melting the sample to produce a molten sample. According to such embodiments, the sample is molten in the detection step and the nuclear spin transitions in the at least one spin half nucleus of the analyte in the molten sample may be detected by liquid-state NMR. Alternatively, the nuclear spin transitions in the at least one spin half nucleus of the analyte in the molten sample may be detected by MRI. According to this last embodiment, at least a portion of the molten sample that includes polarized analyte is administered (e.g., by injection, ingestion, inhalation, etc.) to a subject prior to detection. In certain embodiments (e.g., when the polarizing agent is toxic) the polarized analyte may be separated from the polarizing agent prior to administration. U.S. Pat. No. 6,311,086 (the contents of which are incorporated herein by reference) describes several methods for achieving such a separation (e.g., physical and chemical separation or extraction techniques).

In general, the methods may be used to polarize any analyte. Without limitation, the analyte may be a protein or nucleic acid. In certain embodiments, the analyte may be a protein or nucleic acid that is covalently attached to the polarizing agent. For example, in the case of polarizing agents defined by Formula I, $R^1$, $R^2$, or both $R^1$ and $R^2$ are an analyte (e.g., a protein) covalently attached to the polarizing agent).

Numerous solid-state and liquid-state NMR methods have been developed to study the structures of these biomolecules, e.g., one dimensional techniques, multi-dimensional techniques, including without limitation techniques that rely on NOESY, ROESY, TOCSY, HSQC, HMQC, etc. type polarization transfers and combinations thereof. Any of these techniques and variants thereof may benefit from the enhanced NMR signals that can be provided by the methods described herein. The methods may also be advantageously used to improve the detection of analytes (e.g., metabolites) that are present in a sample at low concentrations (e.g., less than 1 μM, less than 100 nM, less than 10 nM or even less than 1 nM). When the analyte is being used as an imaging agent for an MRI experiment then it will preferably include at least one spin half nucleus with a long $T_1$ relaxation time. This will ensure that the enhancement is not lost by relaxation in between the polarizing and detecting steps. For example, U.S. Pat. No. 6,311,086 describes imaging agents that include spin half nuclei with $T_1$ relaxation times of at least 6 seconds at 310 K in $D_2O$ in a magnetic field of 7 T. It will be appreciated that any of the imaging agents that are described in U.S. Pat. No. 6,311,086 may be used as an analyte in a method described herein. It is also to be understood that any known MRI technique may be used to image the spatial distribution of a polarized analyte once administered to a subject (e.g., see MRI in Practice Ed. by Westerbrook et al., Blackwell Publishing, Oxford, U K, 2005, the contents of which are incorporated herein by reference).

Any spin half nucleus within the analyte may be polarized according to the methods described herein. In one embodiment, the spin half nucleus is a $^1H$ nucleus. In one embodiment, the spin half nucleus is a $^{13}C$ nucleus. In one embodiment, the spin half nucleus is a $^{15}N$ nucleus. In one embodiment, the spin half nucleus is a $^{19}F$ nucleus. The spin half nucleus may be present in the analyte at natural abundance levels. Alternatively, stronger signals may be obtained if the spin half nucleus (e.g., $^{13}C$, $^{15}N$, $^{19}F$, etc.) is enriched at one or more positions within the analyte. A variety of methods are known in the art for enriching one or more sites of an analyte (e.g., a protein, nucleic acid, metabolite, imaging agent, etc.). When the at least one spin half nucleus has a γ-value smaller than that of $^1H$ (e.g., $^{13}C$, $^{15}N$, $^{19}F$, etc.) then in certain embodiments, the step of polarizing may further involve irradiating the frozen sample with radiation having a frequency that causes cross-polarization between a $^1H$ nucleus present in the sample (e.g., without limitation from $^1H_2O$) and the at least one spin half nucleus of the analyte.

The methods described herein may be performed under any magnetic field strength. In one embodiment the field may have a strength in the range of about 0.1 T to about 30 T. For example, some of the experiments that are described herein were performed at 5 T. The radiation for exciting electron spin transitions in the unpaired electron(s) of the polarizing agent at these fields will be in the range of about 2.8 GHz to about 840 GHz. For examples, the radiation in the experiments that are described herein was from a 140 GHz gyrotron.

When studying molten samples (e.g., by liquid-state NMR), the sample may be recycled by freezing the sample, repolarizing the at least one spin half nucleus of the analyte by irradiating the frozen sample with radiation having a frequency that excites electron spin transitions in the polarizing agent, remelting the frozen sample to produce a molten sample, and redetecting nuclear spin transitions in the at least one spin half nucleus of the analyte in the molten sample. This process can be repeated for as many cycles as needed. This can be used, e.g., to signal average NMR signals and thereby further enhance the sensitivity of the NMR experiment. The freezing step can generally be achieved by cooling the sample until it reaches a solid state. In certain embodiments, the sample can be cooled to a temperature of less than about 200 K. For example, the sample may be cooled to a temperature in the range of about 1 K to about 100 K. Some of the experiments that are described herein involved cooling the sample to a temperature of about 100 K. In one embodiment, the freezing step may be completed in less than about 2 minutes, e.g., less than about 1 minute.

In general, once a frozen sample has been polarized, it can be optionally melted prior to signal detection using any suitable method. In certain embodiments, this is achieved by exposing the frozen sample to radiation having a wavelength of less than about 100 μm, e.g., in the range of about 0.5 μm and about 50 μm. In one embodiment the radiation may come from a laser, e.g., a $CO_2$ laser. In another embodiment, the radiation may come from a lamp, e.g., an infra-red lamp. The frozen sample can be exposed to the radiation using an optical fiber. This will typically involve coupling the radiation (e.g., from a laser or lamp) to one end of the fiber, e.g., using a lens. In one embodiment, the sample is within a cylindrical rotor. The rotor can be made of quartz which allows both microwave radiation (e.g., the 140 GHz radiation from a gyrotron) and infra-red radiation (e.g., from a $CO_2$ laser) to reach the sample. In some cases, the quartz rotor does not crack when exposed to multiple freeze-thaw cycles. Finally, the use of a cylindrical rotor can enable the sample to be spun during the melting step (and optionally during other steps including the detecting step) which can significantly improve melting homogeneity and time. In some examples, samples are melted in less than about 1 second.

By way of non-limiting illustration, examples of certain embodiments of the present disclosure are given below.

EXAMPLES

Example 1: Peptide-Based Biradicals for Dynamic Nuclear Polarization of Solid-State Nuclear Magnetic Resonance Spectroscopy The modular and facile generation of nitroxide-based biradical polarizing agents for dynamic nuclear polarization (DNP) solid-state NMR via solid-phase peptide synthesis is described. Four representative peptides were prepared to illustrate the concept, each containing two TOAC spin label amino acids (2,2,6,6-tetramethyl-N-oxyl-4-amino-4-carboxylic acid) at positions i and i+1 or i and i+2, including TOAC-TOAC, acetyl-TOAC-TOAC, TOAC-TOAC-Ser and TOAC-Ser-TOAC. Electron-electron dipolar couplings computed from geometries optimized using broken-symmetry DFT are found to be large, in the ~50-60 MHz range. To assess their utility for potential biomolecular DNP solid-state NMR applications, the four peptide-based biradicals were used as exogenous polarizing agents to enhance $^1H$-$^{13}C$ CP-MAS solid-state NMR spectra of $^{13}C$,$^{15}N$-proline in the usual 6:3:1 $d_8$-glycerol/$D_2O$/$H_2O$ matrix at 600 MHz $^1H$ frequency and temperature of ~100 K. At their optimal concentrations (~10-15 mM), the peptide-based biradicals yielded absolute DNP NMR signal enhancements ranging between ~10 and ~20 and absolute enhancements per unit time ranging between ~5 and ~10, with TOAC-TOAC-Ser providing the highest signal enhancement factors. These results compare favorably with those obtained for the well-established TOTAPOL and AMUPol polarizing agents, which under the same conditions yielded absolute NMR signal enhancements of ~6 and ~30, respectively, and absolute enhancements per unit time of ~3 and ~18, respectively. The fact that such peptide-based biradical polarizing agents displaying an array of physicochemical properties tailored toward different applications, including the possibility to target specific sites in biomolecules by covalent attachment or non-covalent binding, can be readily synthesized makes them a promising tool for DNP solid-state NMR.

Introduction

Dynamic nuclear polarization (DNP) is a powerful technique in increasing the overall sensitivity of solid-state nuclear magnetic resonance (ssNMR) spectroscopy. DNP employs a microwave-driven transfer of polarization, from free electrons to surrounding nuclei, to achieve hyperpolarization in a given magnetic field. While this method has been known since the 1950s, recent technologies have enabled DNP to become coupled to high-field ssNMR with the development of gyrotrons capable of generating high-powered, high-frequency microwaves. In theory, the maximum signal enhancement that may be achieved using DNP is a ratio of the electron to proton Larmor frequencies, $\gamma_e/\gamma_H$~660. Currently, DNP signal enhancements of 30 to 50 have been achieved for biological samples and over 200 in small molecules and materials.

A number of methods have been paired with DNP to optimize the technique for studying small molecules, biological systems and synthetic materials. Low temperatures are employed to maximize the DNP effect by exploiting longer spin relaxation times at low temperatures. Small biradical molecules have been synthesized to serve as an exogenous paramagnetic source and to utilize the cross-effect (CE) mechanism of DNP. Glass-forming solvents, such as glycerol and tetrachloroethane (TCE), are used to dissolve these biradical polarizing agents and to suspend them throughout a sample-of-interest in a cryo-protecting glass. Magic-angle spinning (MAS) ssNMR is employed to study these frozen glasses, with the use of cryogenic probes, to overcome chemical shift anisotropies found in solids and frozen solutions. Recently, additional methods such as systematic biradical design, isotopic deuteration of polarizing agents, fast-spinning MAS, and multi-dimensional NMR experiments have been employed to further enhance this strategy.

Nitroxide radicals are the preferred radical in DNP because they are stable and easily-incorporated into organic syntheses. Nitroxide-based biradicals were developed by synthetically tethering together two 2,2,6,6-tetramethyl-1-piperidinyloxy (TEMPO)-moieties. By fixing the inter-electron distance through biradical design, the efficiency of the CE mechanism of DNP greatly increases, resulting in larger DNP enhancements. Common biradicals include TOTA-POL, AMUPOL and TEKPOL, which can reach DNP enhancements of over 200. Biradicals have been designed to shorten inter-electron distances, to restrain dinitroxide g-tensors in orthogonal orientations, to increase electron relaxation times ($T_{1e}$, $T_{2e}$) and to increase solubilities.

In this example, a new category of nitroxides biradicals based on peptide synthesis and the amino acid derivative TOAC is described. Solid phase peptide synthesis (SPPS) is a popular technique for synthesizing short peptides in a quick and controlled fashion. By using TOAC as a mononitroxide building block, biradical peptides can quickly be synthesized to different inter-nitroxide lengths and amino acid compositions. Herein, four example TOAC-based biradical peptides have been prepared and evaluated: TOAC-TOAC (TT), TOAC-Ser-TOAC (TST), TOAC-TOAC-Ser (TTS) and acetyl-TOAC-TOAC (ATT). In addition, the geometries of these biradicals were evaluated using broken symmetry DFT calculations, their biradical characteristics were investigated by continuous wave (CW), X-band EPR spectroscopy, and their DNP-ssNMR characteristics as polarizing agents were identified.

Materials and Methods

Biradical peptide synthesis: TOAC-based biradical peptides TOAC-TOAC (TT), TOAC-Ser-TOAC (TST), TOAC-TOAC-Ser (TTS), and acetyl-TOAC-TOAC (ATT) were synthesized via Fmoc-based solid-phase peptide synthesis. Briefly, Fmoc-2,2,6,6-tetramethylpiperidine-A-oxyl-4-amino-carboxylic acid (Fmoc-TOAC-OH, Chem-IMPEX, CAS #93372-25-9) was coupled to Wang resin using HATH, HOAt, and DIPEA, dissolved in DMF. The reaction vessel was shaken at room temperature for 24 hr. The Fmoc-protecting group was removed with 20% piperidine/DMF. Subsequent amino acid or TOAC-couplings were then repeated until desired product was prepared. Then, the peptide was cleaved from the resin using 95% TFA/2.5% $H_2O$/2.5% TIS. The filtrate was concentrated under vacuum and re-dissolved in methanol. The crude product was purified by reverse-phase HPLC ($C_{18}$, 50 mM $NH_4CH_3COO$ pH=5.0, 60% $CH_3CN/H_2O$) and lyophilized. Nitroxide-radicals are regenerated by re-dissolving product in 0.5 M $NH_4CH_3COO$ pH 9.5 and let sit overnight at 4° C. Ammonium acetate is removed via HPLC ($C_{18}$, $H_2O$, 60% $CH_3CN/H_2O$). Pure product is lyophilized and stored at 4° C.

Detailed synthetic protocols for TT, TST, TTS, and TTS are described below.

EPR Spectroscopy; Ail spectra were obtained on a Bruker EMXPlus EPR spectrometer (CW, X-band) at room temperature. A standard concentration curve was made using 4-hydroxyl-2,2,6,6-tetramethyl-1-oxyl (TEMPOL, Sigma-Alrich, CAS #2226-96-2) dissolved in 3:2 glycerol/$H_2O$ and packed into a glass capillary. TEMPOL concentrations were confirmed and standardized by UV-Vis spectroscopy. Biradical EPR-profiles are obtained by dissolving activated TOAC-based biradical peptides in methanol at concentrations of approximately 5 mM to 20 mM. Biradical concentrations of DNP samples in 6:3:1 d8-glycerol/$D_2O$/$H_2O$ are determined using the TEMPOL standard curve.

DNP-SSNMR Sample Preparation: AMUPOL was obtained from SATT SUD-EST (Marseille. France). TOTA-POL was purchased from DyNuPol, Inc. (Newton, Mass.). These nitroxides were used as provided by the manufacturer without any further purification, AMUPOL and TOAC-TOAC-Ser were dissolved in 1.25 M 13C,15N-L-proline 3:1 $D_2O/H_2O$ solution. d8-glycerol was added by weight to a final ratio of 6:3:1 d8-glycerol/$D_2O/H_2O$ and a final proline concentration of 0.5 M. Lyophilized TOAC-TOAC and Acetyl-TOAC-TOAC were dissolved in 1.25 M 13C,15N-L-proline, 1 eq. of NaOH, 3:1 $D_2O/H_2O$ solution. d8-glycerol was added by weight to a final ratio of 6:3:1 d8-glycerol/$D_2/H_2O$ and a final proline concentration of 0.5 M. TOTAPOL was dissolved directly into a solution of 0.5 M 13C,15N-L-proline in 6:3:1 d8-glycerol/$D_2O/H_2O$. Biradical concentrations were measured by EPR. Samples were flash frozen and thawed 10 times each. Finally, 23 µL of each solution was pipetted directly into a clean, dry 3.2 mm sapphire rotor and equipped with a silicone plug.

DNP-SSNMR Spectroscopy: All experiments were performed on a Bruker Avance III HD Wide-Bore 14.1 T spectrometer equipped with a 7.2 T gyrotron cryogenic magnet and a 3.2 mm, triple-resonance (HXY), cryogenic LT-MAS probe. Samples were packed into Bruker 3.2 mm sapphire rotors, each with a silicone plug and a zirconium cap. Proline samples were spun at a magic angle frequency of 8000 Hz, with temperatures ranging from 97 K to 107 K. Microwave field power curves were performed for each biradical, to determine the optimal applied MW power for DNP enhancement. Microwaves are set to 145 mA (0.34 V) for AMUPOL, 100 mA (0.10 V) for TOTAPOL, and 115 mM (0.15 V) for TOAC-TOAC. DNP build-up times were measured from a saturation-recovery experiment. $^1H$ $T_1$ relaxation times were measured from two inversion-recovery experiments, one with the microwaves turned on and one with the microwaves turned off. 1D $^1H$-$^{13}C$ cross-polarization experiments were recorded of each sample. For 10 min experiments, recycle delays were set to 1.256×τDNP and number of scans are adjusted to set total experiment time to approximately 10 minutes. Each sample used 4 dummy scans. Signal-to-noise ratios are determined using TOPSPIN 3.5 and are divided by total experiment times (in seconds). Each sample was made from the same proline stock solution, so it was assumed that proline concentrations were identical.

DFT Calculations; Electronic structure calculations were performed using broken-symmetry density functional theory (DFT) at a ωB97X-D/6-31+G* level. C-PCM solvation model with a dielectric constant of 59.3 is also applied. A dielectric constant of 59.3 matches that of 3:2 glycerol/$H_2O$. Calculations of bTUrea and TOTAPOL are used as standards. 1-5 local minimum energy conformations are found in the gas phase for TT, TST, TTS & ATT and the solvent model is applied to each of these. Nitroxide distances and relative orientations are extracted from these structures and weighted averages are determined based on their relative abundances at 100K.

Results and Discussion

The unnatural amino acid 2,2,6,6-tetramethyl-1-oxyl-4-amino-4-carboxylic acid (TOAC) contains a stable nitroxide radical and has been used as an ESR spin label. An Fmoc-protecting group can be added for use in Fmoc-based solid phase peptide synthesis (SPPS). This allows TOAC to be incorporated into a peptide at a specific location to serve as a spin probe. By creating TOAC-based biradical peptides though SPPS, the inter-electron distances, solubilities and geometries of each polarizing agent can be customized by inserting additional amino acids or by functionalizing the C- and/or N-terminus of the peptide (e.g., acetylating the N-terminus).

The established biradicals AMUPOL and TOTAPOL are used as standard polarizing agents in aqueous media. TOTA- POL contains two TEMPO-moieties linked by a 5-atom tether. AMUPOL is the leading biradical for use in aqueous media as the nitroxide flanking methyl groups found in TEMPO, are replaced by spirocyclohexyl groups (FIG. 1). This results in longer $T_{2e}$ relaxation times and increased DNP enhancements. Additionally, AMUPOL has an increased solubility in glycerol-water mixtures than TOTAPOL and other nitroxide biradicals. This higher solubility enables AMUPOL to form a good glass in glycerol-water mixtures and to be compatible with biological systems Four TOAC-based biradical peptides were synthesized by SPPS using Fmoc-TOAC-OH, as described in Scheme 1. TOAC-TOAC (TT) is a short, biradical dipeptide; TOAC-Ser-TOAC contains a spacer amino acid, TOAC-TOAC-Ser (TTS) contains an terminal serine; and acetyl-TOAC-TOAC (ATT) contains an acetylated amide (FIG. 1). TOAC residues were coupled to a solid p-benzyloxybenzyl alcohol resin (Wang resin) using HATU/HOAt coupling reagents in the presence of DIPEA. Following SPPS, nitroxide radicals needed to be regenerated as they were oxidized in the strong acidic conditions required for cleavage. This was accomplished by treatment in 10-molar excess ammonium acetate ($NH_4CH_3COO$) with a pH adjusted to 9.5 for 24 hours. $NH_4CH_3COO$ was then removed through a buffer exchange via HPLC.

glycerol. Inter-nitroxide distances were extracted as the average between the N—N distance and the O—O distance. The electron-electron dipolar coupling constant, $D_{ee}$, was calculated as a function of the inter-nitroxide distance. Angles between $C_2NO$ planes and NO-vectors were also measured. Weighted averages of these properties were calculated using each conformers' abundance at 100 K, using their relative energies (Table 1).

TABLE 1

Internuclear distances and geometries of TOAC-based biradical peptides

| | N-N distance (Å) | O-O distance (Å) | Dipolar coupling constant, $D_{ee}$ (MHz) | Angle between $C_2NO$ planes, $\theta$ | Angle between NO vectors, $\varphi$ |
|---|---|---|---|---|---|
| ATT | 8.747 | 10.96 | 59.7 | 34.8 | 128.9 |
| TST | 9.171 | 10.94 | 56.4 | 48.1 | 89.6 |
| TT  | 9.163 | 11.61 | 50.5 | 28.9 | 163.6 |
| TTS | 9.240 | 11.70 | 49.3 | 35.0 | 160.2 |

TOAC directly bound to TOAC only has a 2-atom linkage between TEMPO-moieties, shorter than any previous nitroxide biradical. This results in short inter-nitroxide distances and, subsequently, large dipolar coupling constants. ATT has the shortest inter-electron distance of 9.265 Å and a dipolar Scheme 1. Synthetic pathway of TOAC-TOAC by solid-peptide synthesis using Wang resin and Fmoc-2,2,6,6-tetramethylpiperidine-N-oxyl-4-amino-4-carboxylic acid (Fmoc-TOAC-OH).

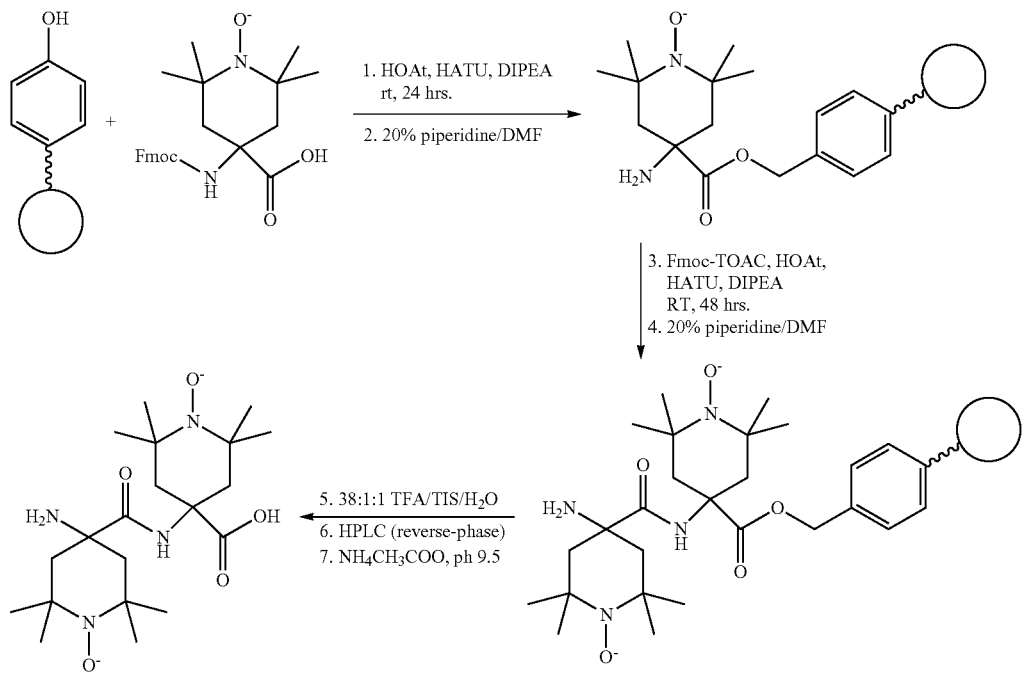

Broken symmetry DFT, ωB97X-D/6-31+G calculations were performed to examine the geometries of the TOAC-based biradical peptides. Broken symmetry DFT was used to break the alpha and beta spin symmetry in order to properly capture the open-shell singlet character. Up to five of the lowest energy conformers were found in the gas phase for each biradical. These geometries were then optimized using a C-PCM solvation model with a dielectric constant of 59.3 was also applied to mimic DNP solvent conditions of 60% coupling constant of 59.7 MHz. In comparison, TOTAPOL has an inter-electron distance of 13.1 Å and $D_{ee}$ of 23.2 MHz, and AMUPOL has an inter-electron distance of 11.61 Å and a $D_{ee}$ of 35.4 MHz. These TOAC-TOAC peptides (TT, TTS, ATT) share similar geometries between inter-electron distance and angles between TEMPO-groups. Also, the short linkage between TOAC residues leads a more restricted geometry. Interestingly, TST has the second shortest inter-nitroxide distance despite having an additional amino acid separating the TEMPO-moieties. This is a result of a hydrogen bond between terminal amine and carboxylic groups, which pulls the TOAC residues together. But the longer backbone will likely result in a larger sampling of orientations with less favorable DNP characteristics.

Room temperature, continuous wave (CW), X-band EPR spectra were collected for each biradical peptide. These spectra all display a signature five-line pattern. 3-lines coincide with a monomeric nitroxide radial due to electron-nitrogen ($^{14}$N) hyperfine coupling ($A_N$) while an additional two are present due to coupled electrons. Biradicals possessing these five-peak spectra can be regarded as having an average exchange integral (J) larger than the $A_N$. Biradicals possessing only 3-peaks are assumed to have J≈$A_N$ (45 MHz). The EPR spectra changes between solvents (methanol, 60% glycerol) because the rate of molecular reorientation depends on the solvent viscosity. Anisotropies present in the g-tensor and $^{14}$N hyperfine tensor results in increased linewidths in viscous solvents. EPR spectra of biradicals dissolved in 60% glycerol are used for determining quantitative electron spin concentrations. Monoradical TEMPOL dissolved in 60% glycerol is used as a standard, with concentrations confirmed by UV-Vis spectroscopy. EPR spectra are collected with a 150 G sweep width, microwave power of 2.000 mW (below the saturation condition), 7.0 s sampling time and 1500 points. The double integration of each sample was recorded and compared to the TEMPOL concentration curve to determine the electron spin concentration. Using this method, a series of samples with increasing biradical concentration are prepared for each TOAC-based biradical peptide, AMUPOL, and TOTAPOL. Between four and six samples are prepared for each biradical, with final dinitroxide concentrations ranging from 5 mM to 30 mM. Each sample was prepared and packed in identical fashion, using the same stock solutions and d8-glycerol to ensure that a final proline concentration of 0.5 M was consistent among each sample. This allowed for the direct comparison of the DNP enhancement and depolarizing effect of each biradical.

$^1$H-$^{13}$C cross-polarization experiments are recorded for each 0.5 M $^{13}$C,$^{15}$N-L-proline sample with varying concentrations of each biradical. DNP enhanced spectra are collected in the presence of microwave irradiation, set at a radical-dependent power level. Spectra in the absence of DNP enhancement are recorded with the microwave irradiation turned off. Microwave-off spectra are collected at a temperature of 97 K and the temperature of microwave-on spectra vary from 101 K to 107 K. These temperature differences are not accounted for when directly comparing the on-to-off signal enhancement, commonly known as the DNP enhancement, $\varepsilon_{DNP}$ (equation 1).

$$\varepsilon_{DNP} = \frac{\text{Intensity } (MW \text{ on})}{\text{Intensity } (MW \text{ off})} - 1 \tag{1}$$

Absolute enhancement, $\varepsilon_{Abs}$, is determined through the signal intensity difference between a biradical-doped sample and an undoped sample of identical proline concentration (equation 2).

$$\varepsilon_{Abs} = \frac{\text{Intensity } (MW \text{ on})}{\text{Intensity } (MW \text{ off})} - 1 \tag{2}$$

$\varepsilon_{Abs}$ values are always smaller than $\varepsilon_{DNP}$ values because the presence of biradical depolarizes nearby nuclei. The amount of depolarization varies with the nature of each biradical, the spin concentration and the MAS frequency. The enhancement profiles of TT, TST, TTS and ATT are shown in FIGS. 2A-2D. 15 mM ATT is found to have the greatest $\varepsilon_{DNP}$ of 48 while 6 mM TTS has the largest $\varepsilon_{Abs}$ of 21. TT and TST have more modest enhancements ($\varepsilon_{DNP}$=25, $\varepsilon_{Abs}$=11-12). These biradical peptides outperform TOT A POL in these same conditions ($\varepsilon_{DNP}$=21, $\varepsilon_{Abs}$=9) but fall behind AMUPOL ($\varepsilon_{DNP}$=107, $\varepsilon_{Abs}$=37). It should be noted that maximum $\varepsilon_{DNP}$ and $\varepsilon_{Abs}$ values do not occur at the same biradical concentration.

Another important factor to determine the optimal sample composition is the DNP build-up time, $\tau_{DNP}$, which is the amount of time required for the enhanced NMR signal to recover under DNP conditions. Low temperatures slow down spin relaxation to where the $^1$H T$_1$ relaxation times of proline, in the absence of any radical, is on the order of 60 s at 100 K. This increases the required delay time between scans and makes signal averaging tedious. The addition of paramagnetic species reintroduces spin relaxation as a function of radical concentration, $\tau_{DNP}$ is a useful measure of $^1$H T$_1$ relaxation and DNP propagation throughout a sample. The optimal recycle delay between scans can then be set to 1.26×$\tau_{DNP}$. DNP build up times decrease with increasing TT, TST, TTS and ATT concentrations (FIGS. 2A-2D).

Neither the $\varepsilon_D$ or $\varepsilon_{Abs}$ properly measures the overall signal gains from DNP in real time. A more accurate measure is a time-adjusted absolute enhancement, $\varepsilon_{Abs-time}$, which predicts the absolute NMR signal enhancement possible with various biradicals by taking into account $\tau_{DNP}$ times and how quickly scans can be recycled (equation 3).

$$\varepsilon_{Abs-time} = \frac{\varepsilon_{Abs}}{\sqrt{1.256 \times \tau_{DNP}}} - 1 \tag{3}$$

Figure 3:
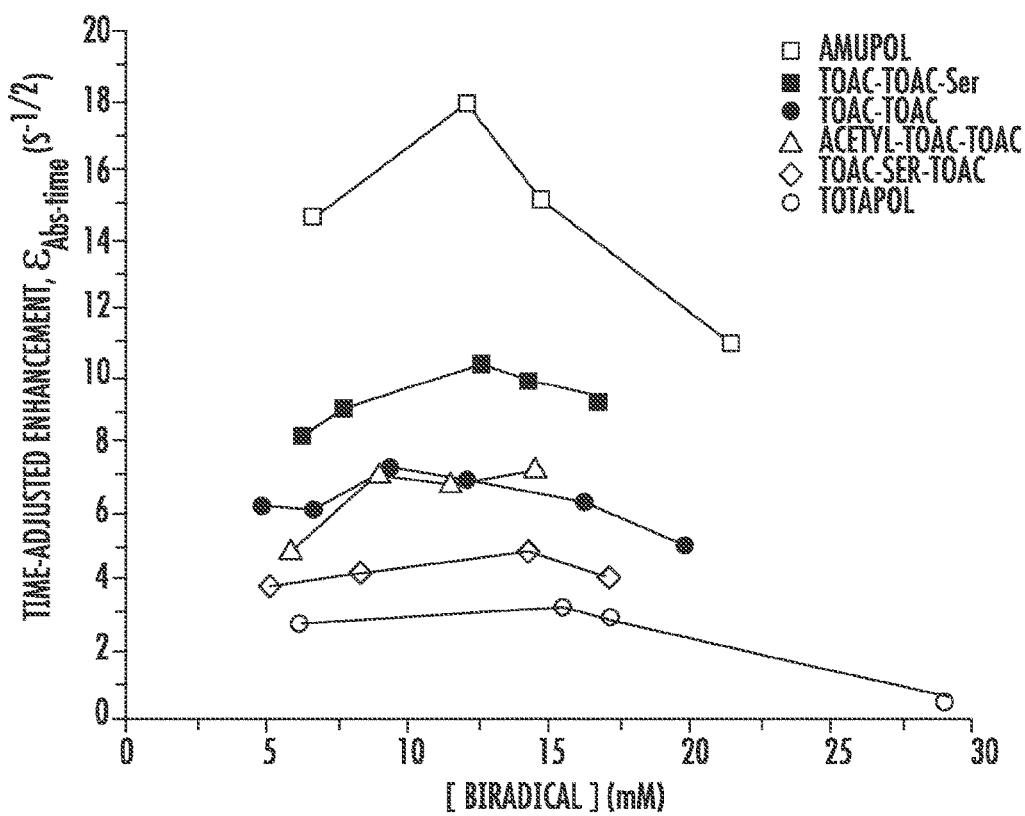
FIG. 3 shows the time-adjusted absolute DNP enhancement profiles for AMUPOL, ATT, TT, TTS, TST, and TOTAPOL, as a function of bi radical concentration.

Time-adjusted absolute enhancement profiles for all six biradical studied here are calculated as a function of biradical concentration (FIG. 3). TOTAPOL has the lowest $\varepsilon_{Abs-time}$ values as small $\varepsilon_{Abs}$ are combined with longer $\tau_{DNP}$ times, for a given spin concentration. TST has only slightly better $\varepsilon_{Abs-time}$ values, obtaining a maximum of 4.8 at 14 mM TST. This is likely because TST and TOTAPOL are similar in size and flexibility. TST has a larger $\varepsilon_{DNP}$ from a large $D_{ee}$ in its lowest energy conformation, but has a long $\tau_{DNP}$ time, relative to other biradicals.

AMUPOL has the largest $\varepsilon_{DNP}$ but its $\varepsilon_{Abs}$ is a factor of 3 smaller, due to large depolarizing effects. AMUPOL is still the best polarizing agent with an $\varepsilon_{Abs-time}$ of 18.0 s$^{1/2}$, but the class of TOAC-TOAC biradical peptides are not far behind. TT has the most modest $\varepsilon_{DNP}$ of 25 but exhibits the least depolarization effects, dropping only by a factor of two with an $\varepsilon_{Abs}$ of 12. Additionally, TT exhibits significantly faster DNP build up times. At similar concentrations of 12 mM biradical, AMUPOL has a $\tau_{DNP}$ of 2.35 s while TT has a $\tau_{DNP}$ of 1.60 s. These phenomena in TT are likely clue to a more even distribution of biradical throughout the sample and better glass formation. ATT has the largest $\varepsilon_{DNP}$ of the biradical peptides at 48 but suffers from large depolarizing effects, with an $\varepsilon_{Abs}$ of only 13. TTS appears to be the best balance among the newly synthesized biradical peptides. TTS has an $\varepsilon_{DNP}$ of 40 and mild depolarizing effects of a factor of two, with an $\varepsilon_{Abs}$ of 19. While $\tau_{DNP}$ times are not as short as TT, TTS has an εAbs-time of 10.3 s$^{1/2}$ due to a higher solubility and better glass formation. Optimal biradical concentrations are determined from these εAbs-time profiles and these DNP properties are summarized in Table 2.

TABLE 2

DNP properties of each polarizing agent at optimal biradical concentrations.

| | AMUPOL | TT | TST | TTS | ATT | TOTAPOL |
|---|---|---|---|---|---|---|
| opt. biradical conc. (mM) | 12.1 | 9.33 | 14.4 | 12.7 | 14.5 | 15.5 |
| $\tau_{DNP}$ (s) | 2.35 | 2.07 | 3.90 | 2.59 | 2.58 | 2.45 |
| $\varepsilon_{DNP}$ | 107.4 | 24.6 | 25.3 | 40.2 | 47.7 | 16.5 |
| $\varepsilon_{Abs}$ | 30.9 | 11.7 | 10.6 | 18.5 | 13.0 | 5.6 |
| $\dfrac{\varepsilon_{Abs}}{\sqrt{1.256 \times \tau_{DNP}}}\left(s^{-\frac{1}{2}}\right)$ | 18.0 | 7.3 | 4.8 | 10.3 | 7.2 | 3.2 |

Figure 4:
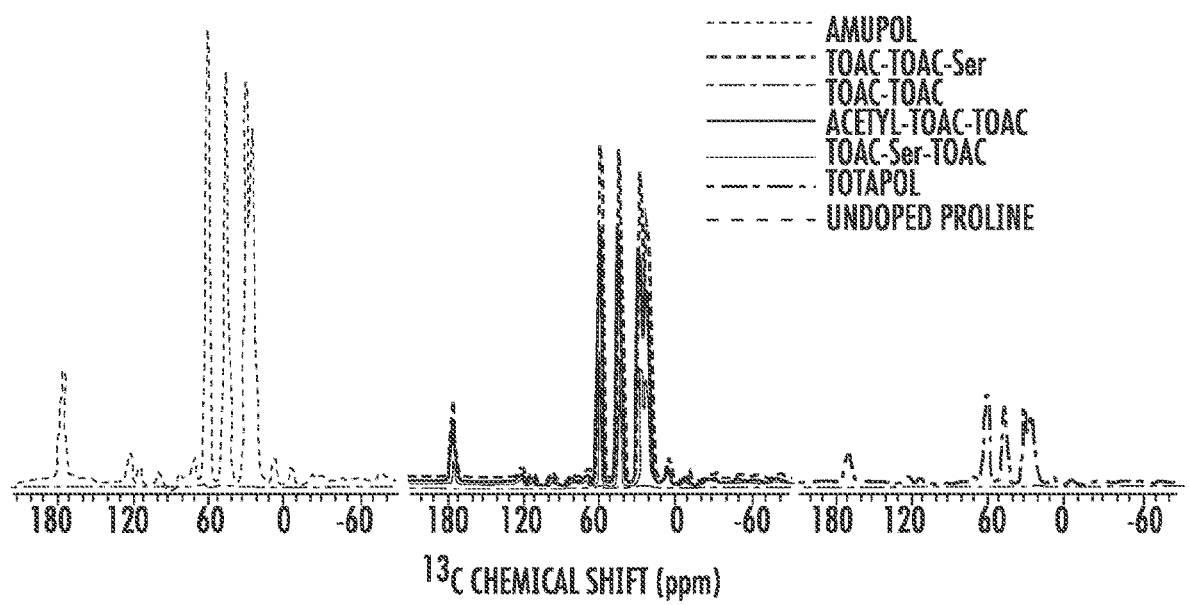
FIG. 4 show's 10-minute $^1H$-$^{13}C$ CP experiments of the optimal concentrations of AMUPOL, TTS, TT, ATT, TST & TOTAPOL with recycle delays set to 1.26×τDNP.

10-minute "real time" experiments were set up to visualize the time-adjusted absolute enhancement (FIG. 4). Recycle delays were set to $1.26 \times \tau_{DNP}$ and the number of scans were adjusted until a total NMR experiment time was approximately 10 minutes. The AMUPOL signal is proportionally set to match the calculated $\varepsilon_{Abs\text{-}time}$. Relative intensities of the remaining biradicals closely match the $\varepsilon_{Abs\text{-}time}$ trend; TT=10.0, TST=4.9, TTS=12.1, ATT=9.0, and TOTAPOL=3.6 (with respect to AMUPOL=18.0.

The four TOAC-containing biradical peptides studied here demonstrate the ability to use SPPS to generate dinitroxide polarizing agents for DNP-ssNMR spectroscopy. These four peptides have various physiochemical characteristics which are tuned by pairing a serine amino acid with TOAC, changing the sequential order of residues, or the acetylation of the N-terminus. This results in large $D_{ee}$ ranging from 49 to 60 MHz, increased solubility of serine containing-peptides, and overall superior DNP utility than TOTAPOL. These biradical peptides also appear to result in better glass formation and a more homogenous distribution throughout the glass, as evidenced by shorter $\tau_{DNP}$ at equal nitroxide concentrations of both AMUPol and TOTAPOL. This is explicitly seen in two human prion protein (huPrP23-144) fibril samples prepared with AMUPol and TTS, at identical biradical concentrations. The sample containing 12 mM TTS has a $\tau_{DNP}$ half that of the sample with 12 mM AMUPol, 2 s to 4 s, which allows for twice the scans in a given experimental time. A logical extension of this study would be the synthesis of additional dinitroxide peptides with sequences and compositions adjusted for desired properties. This would include peptides containing specific amino acid sequences to non-covalently target biomolecules of interest, adding hydrophobic or hydrophilic resides to tune solubilities in aqueous or organic solvents, and covalently binding biradicals to biomolecules through peptide or disulfide bonds. The customizable properties of this new class of nitroxide biradical polarizing agents the potential to expand the techniques used to study numerous systems by DNP-ssNMR.

Experimental Procedures

Protocol for the Synthesis of TOAC-TOAC (TT): In a 10 mL shaker vessel. 202.14 mg of Wang resin was swollen in DCM for 30 mins, then drained and dried under vacuum. Separately, 228.53 mg of Fmoc-TOAC-OH, 117.98 mg of HOAt and 328.73 mg of HATU were dissolved in 3 mL of DMF. Next, 299.3 μL of DIPEA was added, and the solution was mixed for 5 min. Finally, the coupling solution was added to the 10 mL vessel, the vessel was flushed with $N_2$ gas and shaken for 24 hours at RT. The solvent was drained, the resin was washed with DMF (3×) and DCM (3×), then dried under vacuum. A Kaiser test was used to confirm complete coupling. The resin was capped with 32.3 μL acetic anhydride and 27.7 μL pyridine for 30 mins. The solvent was drained, the resin was washed with DMF (3×) and DCM (3×), then dried under vacuum. The resin was then deprotected with 20% piperidine/DMF for 20 min (2×), rinsed with DMF (3×) and DCM (5×), and dried.

The Fmoc-TOAC-OH coupling was then repeated (as described above) and shaken for 48 hours at RT. The Kaiser test was used to confirm complete coupling. The resin was then deprotected with 20% piperidine/DMF (2×), rinsed with DMF (3×) and DCM (5×), and dried. The product, TOAC-TOAC, was cleaved from the resin with 95% TFA, 2.5% TIS and 2.5% $H_2O$. The TFA was collected and concentrated, then the product was precipitated by adding diethyl ether. The product was collected via centrifugation. The product was redissolved in MeOH, purified by reverse-phase HPLC (C18, 50 mM $NH_4CH_3COO$, pH=5.0/$CH_3CN$) and lyophilized.

The TOAC-TOAC was dissolved to a concentration of 50 mM in a solution of 500 mM $NH_4CH_3COO$ pH=9.5. The solution was vortexed to fully dissolve and gently agitated for 24 hours at RT to fully activate. Buffer exchange was performed using reverse-phase HPLC (C18, $H_2O$/$CH_3CN$), and the resulting product was lyophilized.

Figure 5A:
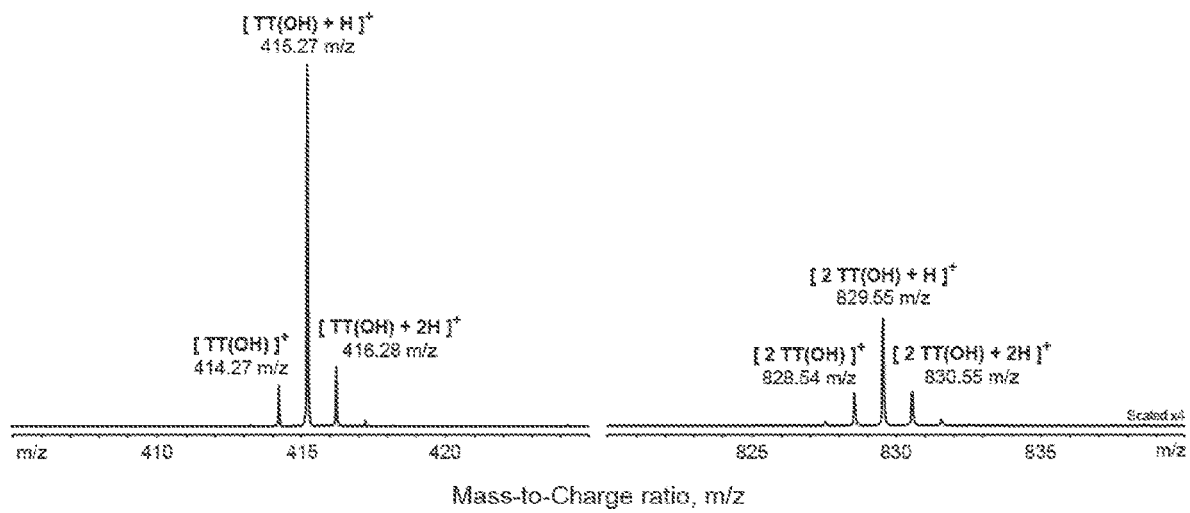
FIG. 5A shows the positive mode electron spray ionization mass spectrometry (ESI-MS) of oxidized TOAC-TOAC, TT(OH). Expected mass: 414.28 m/z. Found masses: 414.27 m/z, 415.27 m/z, 416.28 m/z. 95.6% TT purity.
Figure 5B:
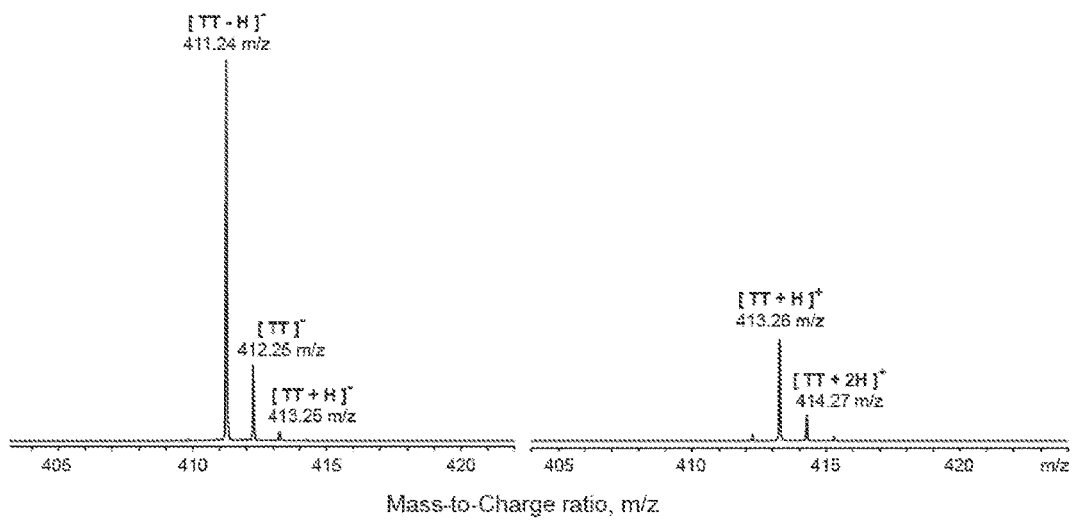
FIG. 5B shows the negative and positive mode ESI-MS of activated, reduced TOAC-TOAC, TT. Expected mass: 412.27 m/z. Found masses: 411.24 m/z, 412.25 m/z, 413.25 m/z, 413.26 m/z, 414.27 m/z. 90.4% TT purity.
Figure 5C:
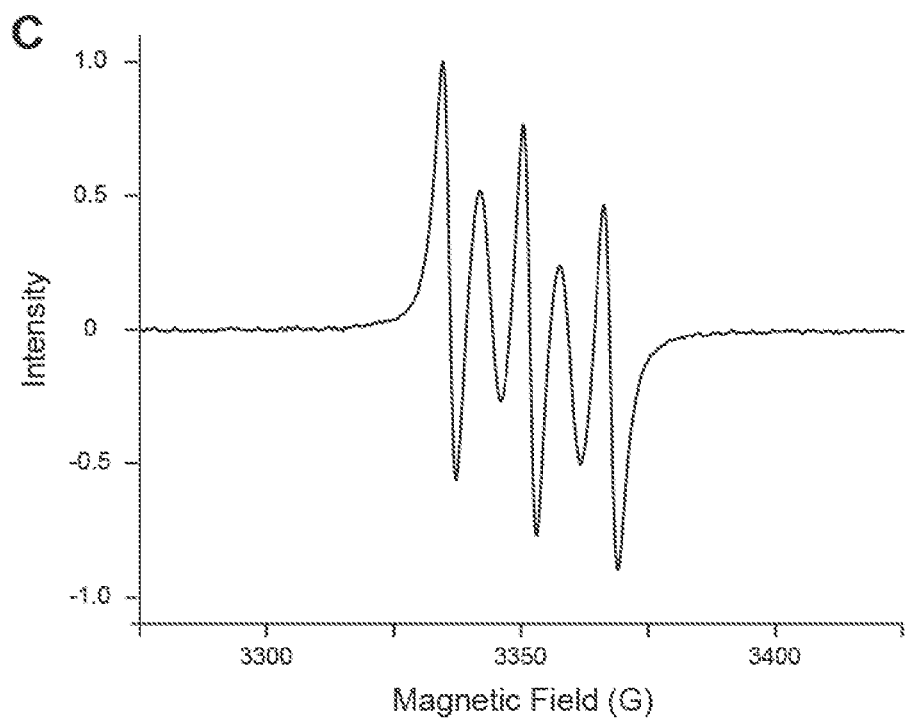
FIG. 5C shows the continuous wave, X-band electron paramagnetic resonance (EPR) spectrum of activated TOAC-TOAC (500 mM $NH_4CH_3COO$ pH 9.5, 50 mM TT) diluted to 5 mM TT in methanol. Microwave power=2.0 W, sampling time=7.0 s, time constant=1.28 s, 4 scans.
Figure 5D:
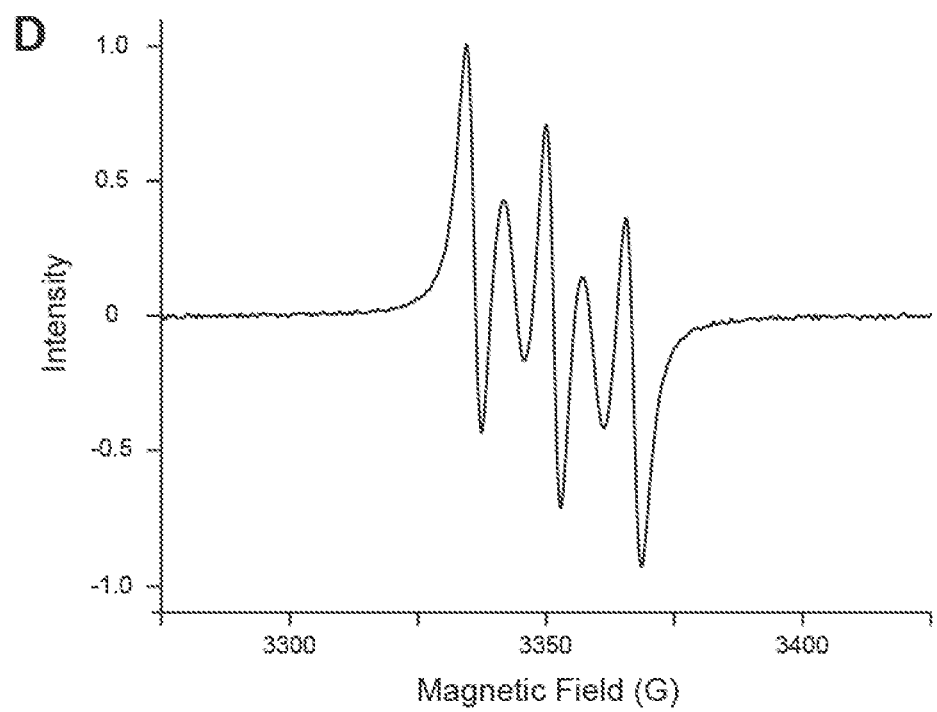
FIG. 5D show's the continuous wave, X-band EPR spectrum of purified TOAC-TOAC by reverse-phase HPLC ($C_{18}$, $H_2O$/$CH_3CN$) and lyophilization. Dissolved in methanol. Microwave power=2.0 W, sampling time=7.0 s, time constant=1.28 s, 4 scans.

TT was fully characterized by Electron Spray Ionization (ESI) Mass Spectrometry and Electron Paramagnetic Resonance (EPR) Spectroscopy. FIG. 5A shows positive mode ESI-MS of oxidized TOAC-TOAC, TT(OH). Expected mass: 414.28 m/z. Found masses: 414.27 m/z, 415.27 m/z, 416.28 m/z, 95.6% TT purity. FIG. 5B shows negative and positive mode ESI-MS of activated, reduced TOAC-TOAC, TT. Expected mass: 412.27 m/z. Found masses: 411.24 m/z, 412.25 m/z, 413.25 m/z, 413.26 m/z, 414.27 m/z. 90.4% TT purity. FIG. 5C shows continuous wave, X-band EPR spectrum of activated TOAC-TOAC (500 mM $NH_4CH_3COO$ pH 9.5, 50 mM TT) diluted to 5 mM TT in methanol. Microwave power=2.0 W, sampling time=7.0 s, time constant=1.28 s, 4 scans. FIG. 5T) shows continuous wave, X-band EPR spectrum of purified TOAC-TOAC by reverse-phase HPLC (C18, $H_2O$/$CH_3CN$) and lyophilization. Dissolved in methanol. Microwave power=2.0 W, sampling time=7.0 s, lime constant=1.28 s, 4 scans.

Protocol for the Synthesis of TOAC-Ser-TOAC (TST): In a 10 mL shaker vessel, 207.42 mg of Wang resin was swollen in DCM for 30 mins, then drained and dried under vacuum. Separately, 233.08 mg of Fmoc-TOAC-OH, 121.33 mg of HOAt and 336.56 mg of HATH were dissolved in 3 mL of DMF. Next, 296.3 μL of DIPEA were added and the solution was mixed for 5 min. Finally, the coupling solution was added to the 10 mL vessel, the vessel was flushed with N$_2$ gas and shaken for 24 hours at RT. The solvent was drained, wash the resin with DMF (3×) and DCM (3×), then dry under vacuum. Use Kaiser test to confirm complete coupling. The resin was capped with 32.1 μL acetic anhydride and 27.4 μL pyridine for 30 mins. The solvent was drained, the resin was washed with DMF (3×) and DCM (3×), then dried under vacuum. The resin was deprotected with 20% piperidine/DMF for 20 min (2×), rinsed with DMF (3×) and DCM (5×), and dried.

325.16 mg of Fmoc-Ser(tBu)-OH and 337.57 mg of HATU were dissolved in 3 mL of DMF. Next, 296.3 μL of DIPEA was added and the solution was mixed for 5 min. Finally, the coupling solution was added to the 10 mL vessel. The vessel was flushed with N$_2$ gas and shaken for 21 hours at RT. The solvent was drained, and the resin was washed with DMF (3×) and DCM (3×), then dried under vacuum. A Kaiser test was used to confirm complete coupling. The resin was deprotected with 20% piperidine/DMF (2×), rinsed with DMF (3×) and DCM (5×) and dried.

The Fmoc-TOAC-OH coupling was then performed (as described above) and shaken for 48 hours at RT. A Kaiser test was used to confirm complete coupling. The resin was deprotected with 20% piperidine/DMF (2×), rinsed with DMF (3×) and DCM (5×) and dried. The product, TOAC-Ser-TOAC, was cleaved from the resin with 95% TFA, 2.5% TIS and 2.5% H$_2$O. The product was collected and concentrated the TFA, then precipitated by adding diethyl ether. The product was collected via centrifugation. The product was then redissolved in MeOH, purified by reverse-phase HPLC (C18, 50 mM NH$_4$CH$_3$COO pH=5.0/CH$_3$CN) and lyophilized.

TST was dissolved to a concentration of 50 mM in a solution of 500 mM NH$_4$CH$_3$COO pH=9.5. The solution was vortexed to fully dissolve the TTS, and the solution was gently agitated for 24 hours to fully activate. Buffer exchange was performed using reverse-phase HPLC (C18, H$_2$O/CH$_3$CN) and the resulting product was lyophilized.

Figure 6A:
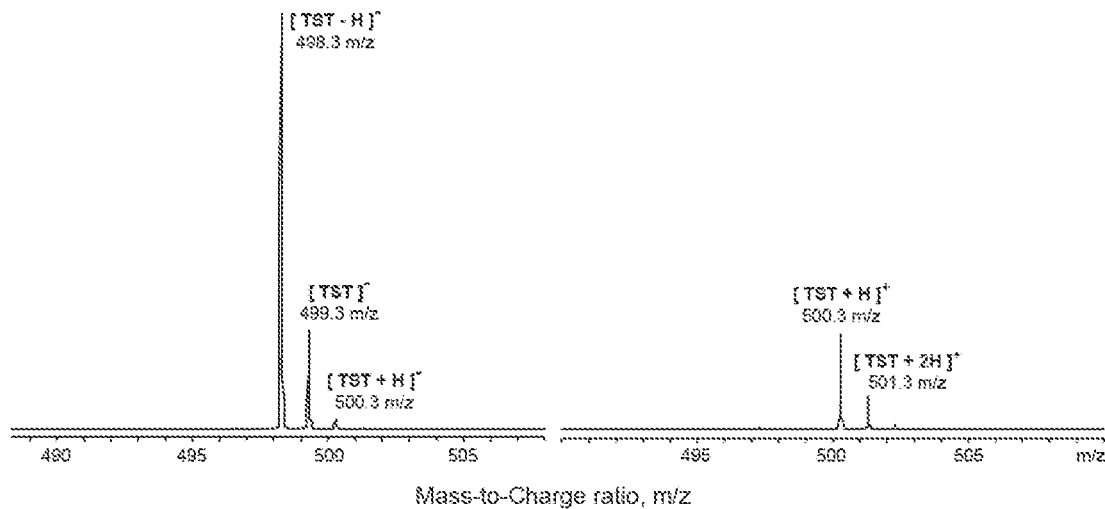
FIG. 6A shows negative mode ESI-MS of reduced TOAC-Ser-TOAC, TST. Expected mass: 499.30 m/z. Found masses: 498.3 m/z, 499.3 m/z, 500.3 m/z. 91.3% TST purity.
Figure 6B:
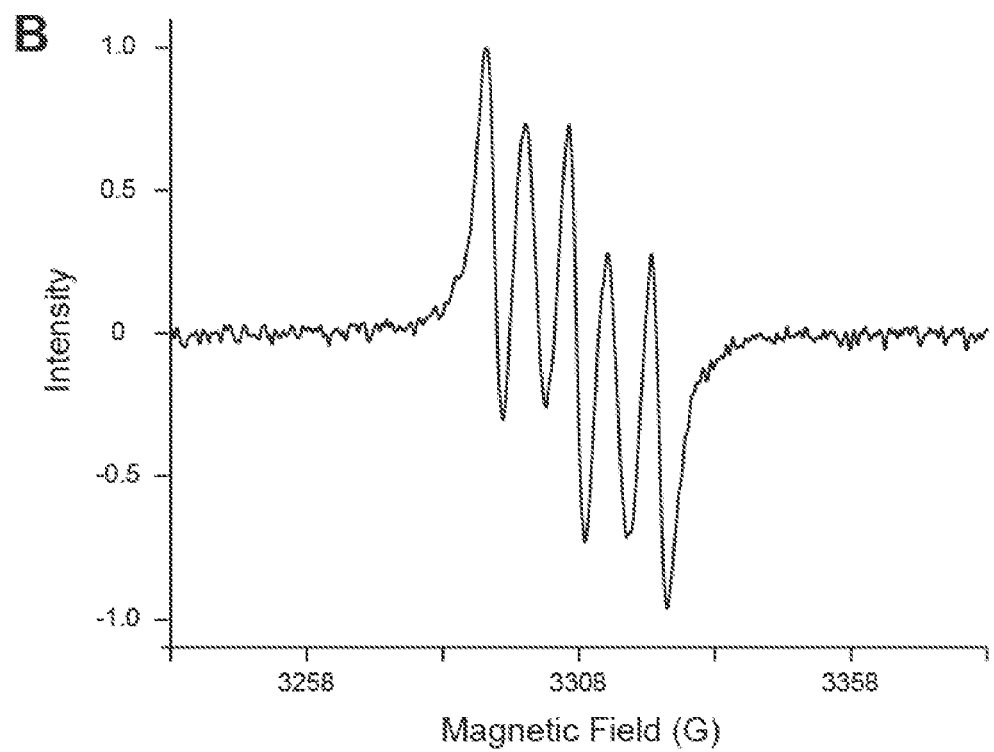
FIG. 6B shows continuous wave, X-band EPR spectrum of activated TOAC-Ser-TOAC (500 mM $NH_4CH_3COO$ pH 9.5, 50 mM TST) diluted to 5 mM TST in methanol. Microwave power=2.0 W, sampling time=7.0 s, time constant=1.28 s, 128 scans.

TST was fully characterized by Electron Spray Ionization (ESI) Mass Spectrometry and Electron Paramagnetic Resonance (EPR) Spectroscopy. FIG. 6A show's negative mode ESI-MS of reduced TOAC-Ser-TOAC, TST. Expected mass: 499.30 m/z. Found masses: 498.3 m/z, 499.3 m/z, 500.3 m/z. 91.3% TST purity. FIG. 6B shows continuous wave, X-band EPR spectrum of activated TOAC-Ser-TOAC (500 mM NH$_4$CH$_3$COO pH 9.5, 50 mM TST) diluted to 5 mM TST in methanol. Microwave power=2.0 W, sampling time=7.0 s, time constant=1.28 s, 128 scans.

Protocol for the Synthesis of TOAC-TOAC-Ser (TPS); In a 10 mL shaker vessel, 333.6 mg of Fmoc-Ser(tBu)-Wang resin (0.51 meq/g) was swollen in DCM for 30 mins, then drained and dried under vacuum. Separately, 225.98 mg of Fmoc-TOAC-OH, 115.46 mg of HOAt and 325.15 mg of HATU were dissolved in 3 mL of DMF. Next, 296.3 μL of DIPEA was added and the solution was mixed for 5 min. Finally, the coupling solution was added to the 10 mL vessel, to the vessel was flushed with N$_2$ gas and shaken for 24 hours at RT. The solvent was drained, and the resin was washed with DMF (3×) and DCM (3×), then dried under vacuum. A Kaiser test was used to confirm complete coupling. The resin was capped with 35.8 μL acetic anhydride and 30.5 μL pyridine for 30 mins. The solvent was drained, and the resin was washed with DMF (3×) and DCM (3×), then dried under vacuum. The resin was deprotected with 20% piperidine/DMF for 20 min (2×), rinsed with DMF (3×) and DCM (5×) and dried.

The Fmoc-TOAC-OH coupling was repeated (as described above) and shaken for 48 hours at RT. A Kaiser test was used to confirm complete coupling. The resin was deprotected with 20% piperidine/DMF (2×), rinsed with DMF (3×) and DCM (5×) and dried. The product, TOAC-TOAC-Ser, was cleaved from the resin with 95% TFA, 2.5% TIS and 2.5% LEO. The product was collected and the TFA was concentrated, then the product was precipitated by adding diethyl ether. The product was collected via centrifugation. The product was redissolved in MeOH, purified by reverse-phase HPLC (C18, 50 mM NH$_4$CH$_3$COO pH=5.0/CH$_3$CN) and lyophilized.

TOAC-TOAC-Ser was dissolved to a concentration of 50 mM in a solution of 500 mM NH$_4$CH$_3$COO pH=9.5. The solution was vortexed to fully dissolve the TTS, and gently agitated for 24 hours to fully activate. Buffer exchange was performed using reverse-phase HPLC (C18, H$_2$O/CH$_3$CN) and the resulting product was lyophilized.

Figure 7A:
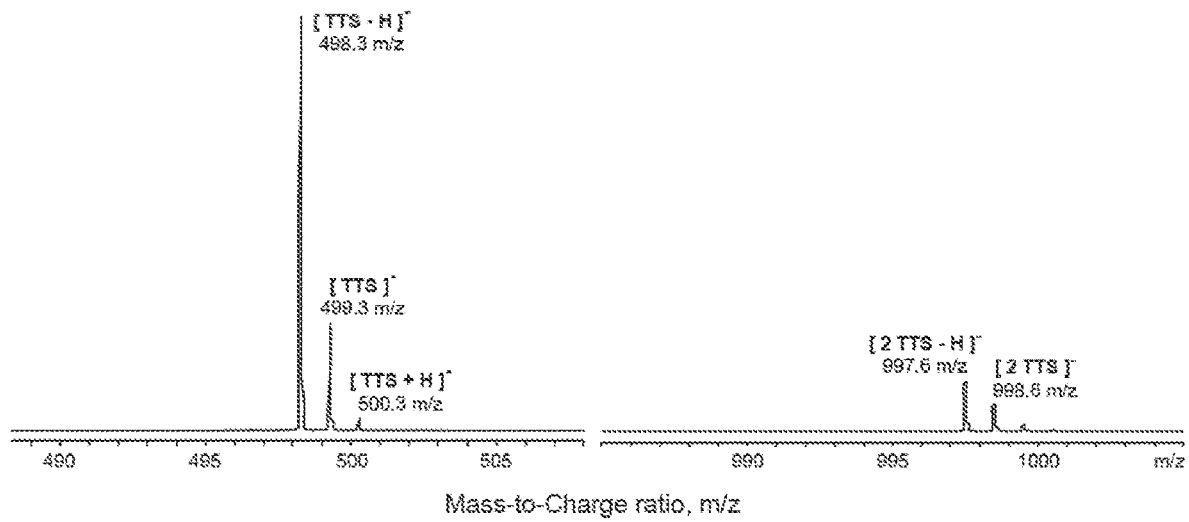
FIG. 7A shows negative mode ESI-MS of reduced TOAC-TOAC-Ser, TTS. Expected mass: 499.30 m/z. Found masses: 498.3 m/z, 499.3 m/z, 500.3 m/z. 91.3% TST purity.
Figure 7B:
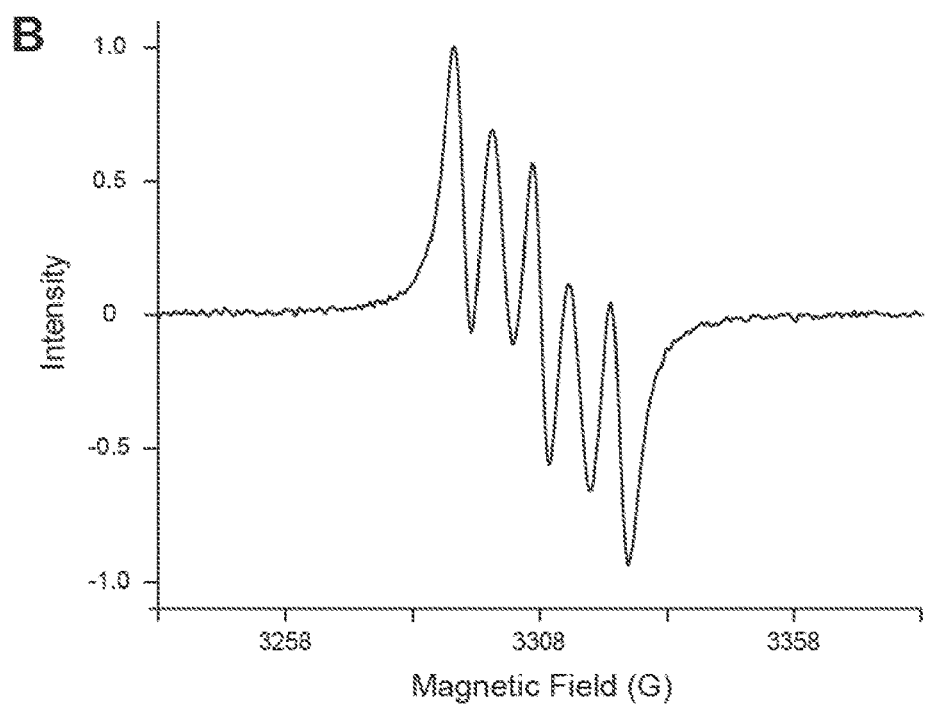
FIG. 7B show's continuous wave, X-band EPR spectrum of activated TOAC-TOAC-Ser (500 mM $NH_4CH_3COO$ pH 9.5, 50 mM TST) diluted to 5 mM TTS in methanol. Microwave power=2.0 W, sampling time=7.0 s, time constant=1.28 s, 128 scans.

TTS was fully characterized by Electron Spray Ionization (ESI) Mass Spectrometry and Electron Paramagnetic Resonance (EPR) Spectroscopy. FIG. 7A shows negative mode ESI-MS of reduced TOAC-TOAC-Ser, TTS. Expected mass: 499.30 m/z. Found masses: 498.3 m/z, 499.3 m/z, 500.3 m/z. 91.3% TST purity. FIG. 7B shows continuous wave, X-band EPR spectrum of activated TOAC-TOAC-Ser (500 mM NH$_4$CH$_3$COO pH 9.5, 50 mM TST) diluted to 5 mM TTS in methanol. Microwave power=2.0 W, sampling time=7.0 s, time constant=1.28 s, 128 scans.

Protocol for the Synthesis of Acetyl-TOAC-TOAC (ATT): In a 10 ml, shaker vessel, 207.76 mg of Wang resin was swollen in DCM for 30 mins, then drain and dry under vacuum. Separately, 228.69 mg of Fmoc-TOAC-OH, 118.30 mg of HOAt and 330.49 mg of HATH were dissolved in 3 ml, of DMF. Next, 302.8 μL of DIPEA was added, and the solution was mixed for 5 min. Finally, the coupling solution was added to the 10 mL vessel, the vessel was flushed with N$_2$ gas and shaken for 24 hours at RT. The solvent was drained, the resin was washed with DMF (3×) and DCM (3×), then dried under vacuum. A Kaiser test was used to confirm complete coupling. The resin was capped with 35.8 μL acetic anhydride and 30.5 μL pyridine for 30 mins. The solvent was drained, and the resin was washed with DMF (3×) and DCM (3×), then dried under vacuum. The resin was deprotected with 20% piperidine/DMF for 20 min (2×), rinsed with DMF (3×) and DCM (5×) and dried.

The Fmoc-TOAC-OH coupling was then repeated (as described above) and shaken for 48 hours at RT. A Kaiser test was used to confirm complete coupling. The resin was deprotected with 20% piperidine/DMF (2×), rinsed with DMF (3×) and DCM (5×) and dried.

Next, 32.8 μL acetic anhydride and 485 μL triethylamine in 3 mL DMF were added to the shaker vessel, and the solution was shaken for 4 hours at RT. This procedure was repeated and a Kaiser test was then used to confirm complete coupling. The resin was then rinsed with DMF (3×) and DCM (5×) and dried.

The product, acetyl-TOAC-TOAC, was cleaved from the resin with 95% TFA, 2.5% TIS and 2.5% H$_2$O. The product was collected and the TFA was concentrated, then the product was precipitated by adding diethyl ether. The product was collected via centrifugation. Then, the product was redissolved in MeOH, purified by reverse-phase HPLC (C18, 50 mM NH$_4$CH$_3$COO pH=5.0/CH$_3$CN) and lyophilized.

The product was dissolved to a concentration of 50 mM in a solution of 500 mM NH$_4$CH$_3$COO pH=9.5. The solution was vortexed to fully dissolve the product and then gently agitate for 24 hours to fully activate. Buffer exchange was performed using reverse-phase HPLC (C18, H$_2$O/CH$_3$CN) and the resulting product was lyophilized.

Figure 8A:
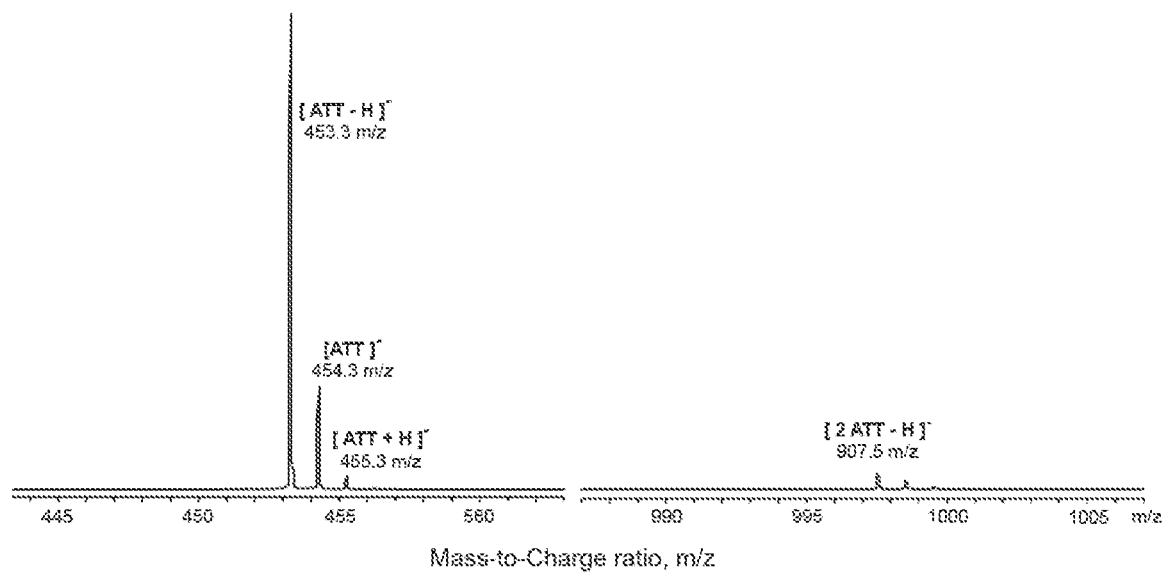
FIG. 8A shows negative mode ESI-MS of reduced Acetyl-TOAC-TOAC, ATT. Expected mass: 454.28 m/z. Found masses: 453.3 m/z, 454.3 m/z, 455.3 m/z, 907.5 m/z, 908.5 m/z. 95.1% ATT purity.
Figure 8B:
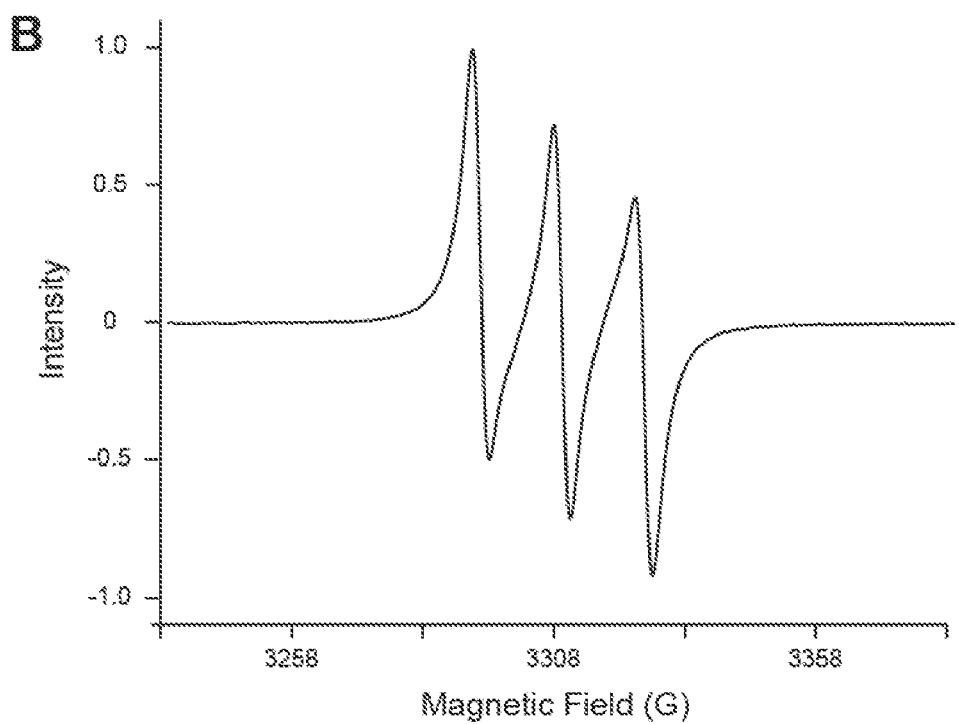
FIG. 8B shows continuous wave, X-band EPR spectrum of activated Acetyl-TOAC-TOAC in methanol. Microwave power=2.0 W, sampling time=7.0 s, time constant=1.28 s, 128 scans.

ATT was fully characterized by Electron Spray Ionization (ESI) Mass Spectrometry and Electron Paramagnetic Resonance (EPR) Spectroscopy. FIG. 8A shows negative mode ESI-MS of reduced Acetyl-TOAC-TOAC, ATT. Expected mass: 454.28 m/z. Found masses: 453.3 m/z, 454.3 m/z, 455.3 m/z, 907.5 m/z, 908.5 m/z. 95.1% ATT purity. FIG. 8B shows continuous wave, X-band EPR spectrum of activated Acetyl-TOAC-TOAC in methanol. Microwave power=2.0 W, sampling time=7.0 s, time constant=1.28 s, 128 scans.

Preparation of $^{13}$C, $^{13}$N-L-Proline Samples for DNP-SSNMR: AMUPOL was obtained from SATT SUD-EST (Marseille, France). TOTAPOL was purchased from DyN-uPol, Inc. (Newton, Mass.). These nitroxides were used as provided by the manufacturer without any further purification. TOAC-based biradical peptides (TT, TST, TTS, ATT) were purified by HPLC, lyophilized, and used as dry powder.

AMUPOL and ITS were dissolved in 1.25 M $^{13}$C,$^{15}$N-L-proline 3:1 D$_2$O/H$_2$O solution. d8-glycerol was added by weight to a final ratio of 6:3:1 d8-glycerol/D$_2$O/H$_2$O and a final proline concentration of 0.5 M. Dry TT and ATT were dissolved in 1.25 M 13C, 15N-L-proline, 1 molar eq. of NaOH, 3:1 D$_2$O/H$_2$O solution. d8-glycerol was added by weight to a final ratio of 6:3:1 dB-glycerol/D$_2$O/H$_2$O and a final proline concentration of 0.5 M. TOTAPOL was dissolved directly into a solution of 0.5 M 13C,15N-L-proline in 6:3:1 d8-glycerol/D$_2$O/H$_2$O.

For EPR spectroscopy, 25 μL of each solution are loaded into a sealed glass capillary using a Hamilton syringe. Biradical concentrations were then determined by EPR. Samples were flash frozen and thawed 10 times each. Finally, 23 μL of each solution was pipetted directly into a clean, dry 3.2 mm sapphire rotor and equipped with a silicone plug.

Figure 9:
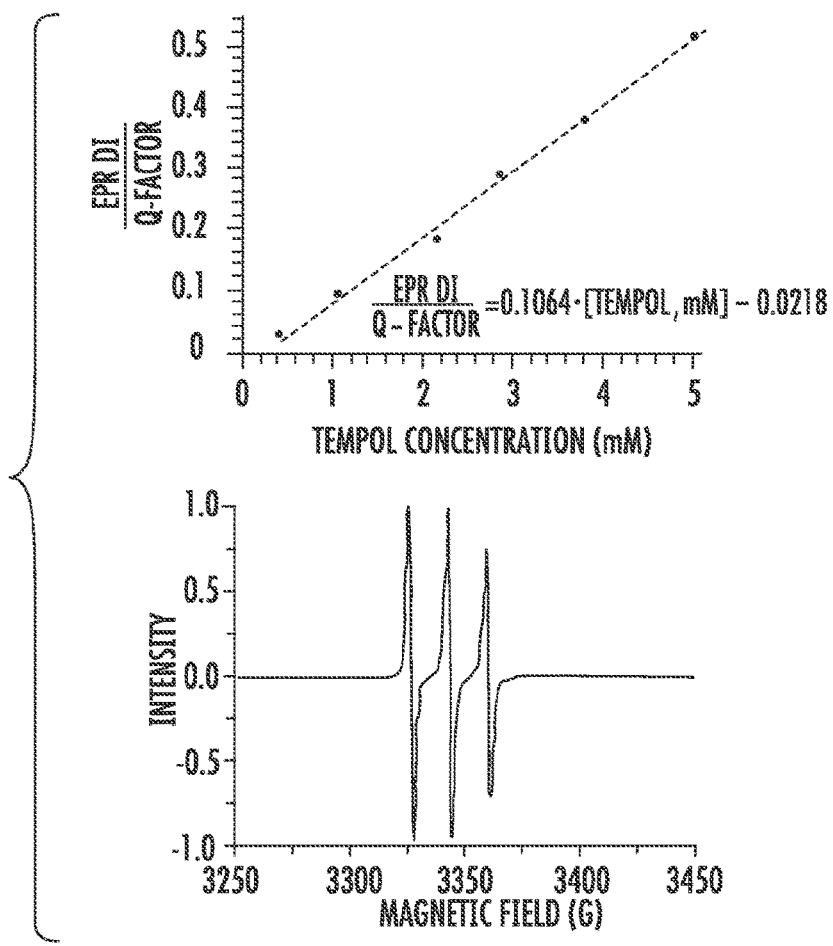
FIG. 9 shows the use if EPR spectroscopy to determine nitroxide concentration. 4-hydroxy-2,2,6,6-tetramethylpiperidine-1-oxyl (TEMPOL, 172.24 g/mol) was dissolved in 3:2 glycerol/$H_2O$. Concentrations were confirmed and standardized by UV-Vis spectroscopy (λ=240 nm). EPR spectroscopy was performed on an X-band, Bruker EMX-Plus spectrometer at room temperature, EPR parameters: center field=3350 G, microwave power=2.0 W, sampling time=7.0 s, time constant=1.28 s, 4 scans. Double integration of the EPR spectrum and the Q-factor of the resonator was used to determine the electron-spin concentration.

FIG. 9 shows the use of EPR spectroscopy to determine nitroxide concentration. 4-hydroxy-2,2,6,6-tetramethylpiperidine-1-oxyl (TEMPOL, 172.24 g/mol) was dissolved in 3:2 glycerol/H$_2$O. Concentrations were confirmed and standardized by UV-Vis spectroscopy (λ=240 nm). EPR spectroscopy was performed on an X-band, Bruker EMX-Plus spectrometer at room temperature. EPR parameters: center field=3350 G, microwave power=2.0 W, sampling time=7.0 s, time constant=1.28 s, 4 scans. Double integration of the EPR spectrum and the Q-factor of the resonator was used to determine the electron-spin concentration.

Figure 10:
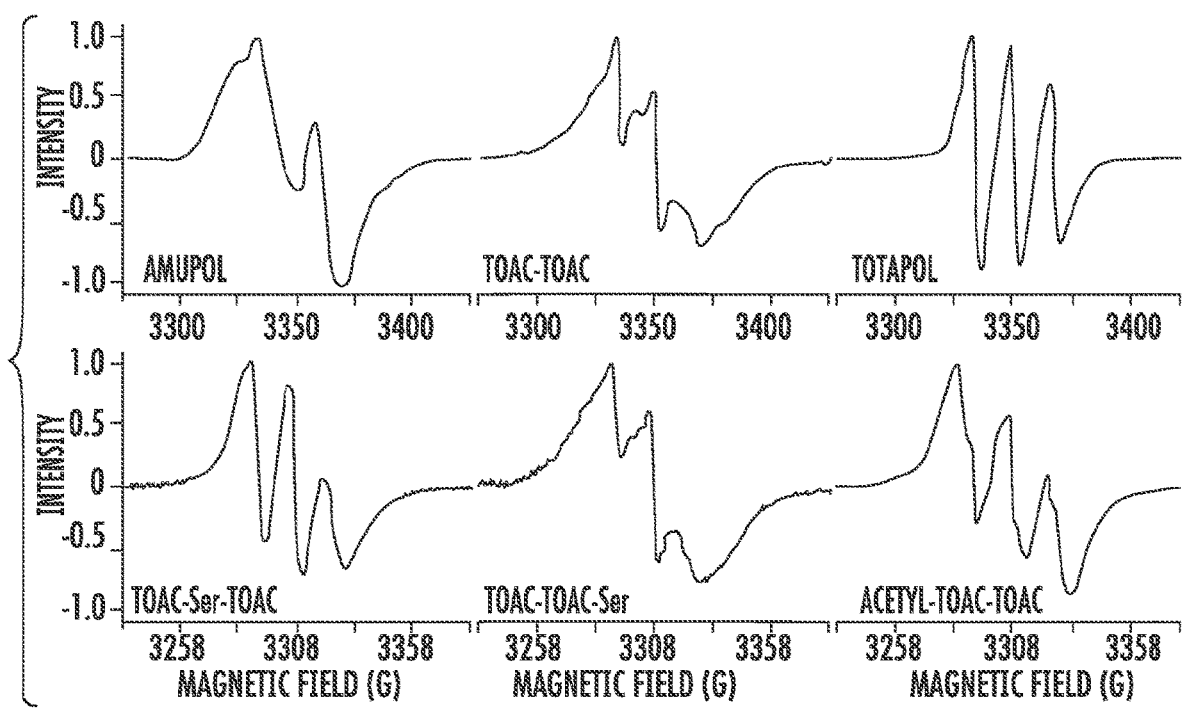
FIG. 10 shows the EPR spectra of biradical DNP samples. 12 mM AMUPOL, 16 mM TOAC-TOAC, 15 mM TOTAPOL, 17 mM TOAC-Ser-TOAC, 17 mM TOAC-TOAC-Ser and 16 mM Acetyl-TOAC-TOAC biradicals were prepared in 6:3:1 $d^8$-glycerol/$D_2O$/$H_2O$ (v/v/v) with 0.5 M $^{13}C$,$^{15}N$-L-proline. EPR spectroscopy was performed on a continuous wave, X-band, Bruker EMX-Plus spectrometer at room temperature. EPR parameters: center field=3350 or 3308 (different cavities) G, microwave power=2.0 W, sampling time=7.0 s, time constant=1.28 s, 4 scans. Signals were scaled to equal intensity for clarity.

FIG. 10 show's the EPR spectra of biradical DNP samples. 12 mM AMUPOL, 16 mM TOAC-TOAC, 15 mM TOTAPOL, 17 mM TOAC-Ser-TOAC, 17 mM TOAC-TOAC-Ser and 16 mM Acetyl-TOAC-TOAC biradicals were prepared in 6:3:1 d$^8$-glycerol/D$_2$O/H$_2$O (v/v/v) with 0.5 M $^{13}$C, $^{15}$N-L-proline. EPR spectroscopy was performed on a continuous wave, X-band, Bruker EMX-Plus spectrometer at room temperature. EPR parameters: center field=3350 or 3308 (different cavities) G, microwave power=2.0 W, sampling time=7.0 s, time constant=1.28 s, 4 scans. Signals were scaled to equal intensity for clarity.

Preparation of $^{13}$C,$^{15}$N-wt-huPrP23-144 Samples for DNP-SSNMR: $^{13}$C,$^{15}$N-wt-huPrP23-144 was expressed and purified based on previously described procedures. Fibrils were prepared using 2% wt-seed with slow inversion at 25° C. for 16 hrs. Prion fibrils were pelleted by centrifugation at 16.1 ref and 4° C. Excess buffer was removed and the fibril pellet were washed with 6:3:1 d8-glycerol/D$_2$O/H$_2$O. Pellets were incubated in 12 mM/AMUPOL or 12 mM TTS in 6:3:1 dB-glycerol/D$_2$O/H$_2$O for 48 hrs. at 4° C. Prion fibrils were collected via ultracentrifugation (5×10$^5$ ref, 4° C.) and washed again with 12 mM biradical solution. Fibrils were packed into 3.2 mm sapphire rotors using a swinging bucket tabletop centrifuge (3000 ref, 4° C.). Rotors were equipped with a silicone plug and a drive cap.

Dynamic Nuclear Polarization (BNP) Solid-State Nuclear Magnetic Resonance (SSNMR) Spectroscopy: All experiments were performed on a Brisker Avance III HD Wide-Bore 14.1 T spectrometer equipped with a 7.2 T gyrotron cryogenic magnet and a 3.2 mm, triple-resonance (HXY), cryogenic LT-MAS probe. Samples were packed into Bruker 3.2 mm sapphire rotors, each with a silicone plug and a zirconium cap. Sapphire rotors were spun with liquid nitrogen cooled gases to achieve ultimate low temperatures of 97 K. Constant microwave irradiation were applied to the sample through a corrugated waveguide at a set microwave power based on the nature of the polarizing agent.

Proline samples and prion samples were spun at magic angle frequencies of 8 kHz and 12 kHz, respectively, at temperatures ranging from 97 K to 107 K. Microwave powers were set to 0.34 V for AMUPOL, 0.10 V for TOTAPOL, 0.16 V for TT, 0.14 V for TTS, 0.12 V for TST, and 0.14 V for ATT.

DNP build-up times, τDNP, were measured from a saturation-recovery experiment. $^1$H T1 relaxation times were measured from two inversion-recovery experiments, one with the microwaves turned on and one with the microwaves turned off. 1D 1H-13C cross-polarization experiments are recorded of each sample. For 10 min experiments, recycle delays are set to 1.256×τDNP and number of scans are adjusted to set total experiment time to approximately 10 minutes.

Figure 11A:
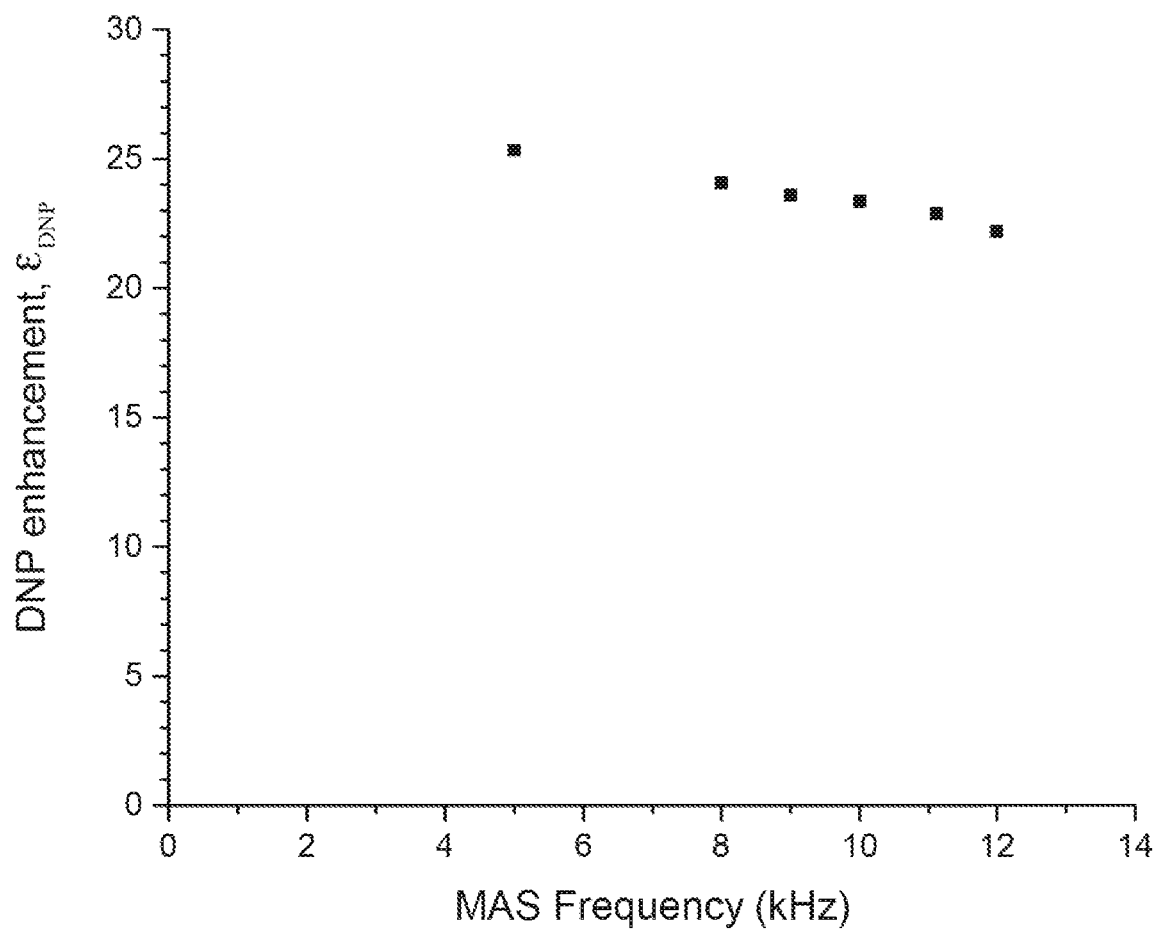
FIG. 11A shows DNP enhancements as a function of magic angle spinning (MAS) frequency from 5 kHz to 12 kHz, where microwave-on spectra are compared to microwave-off spectra at the same spinning speed.
Figure 11B:
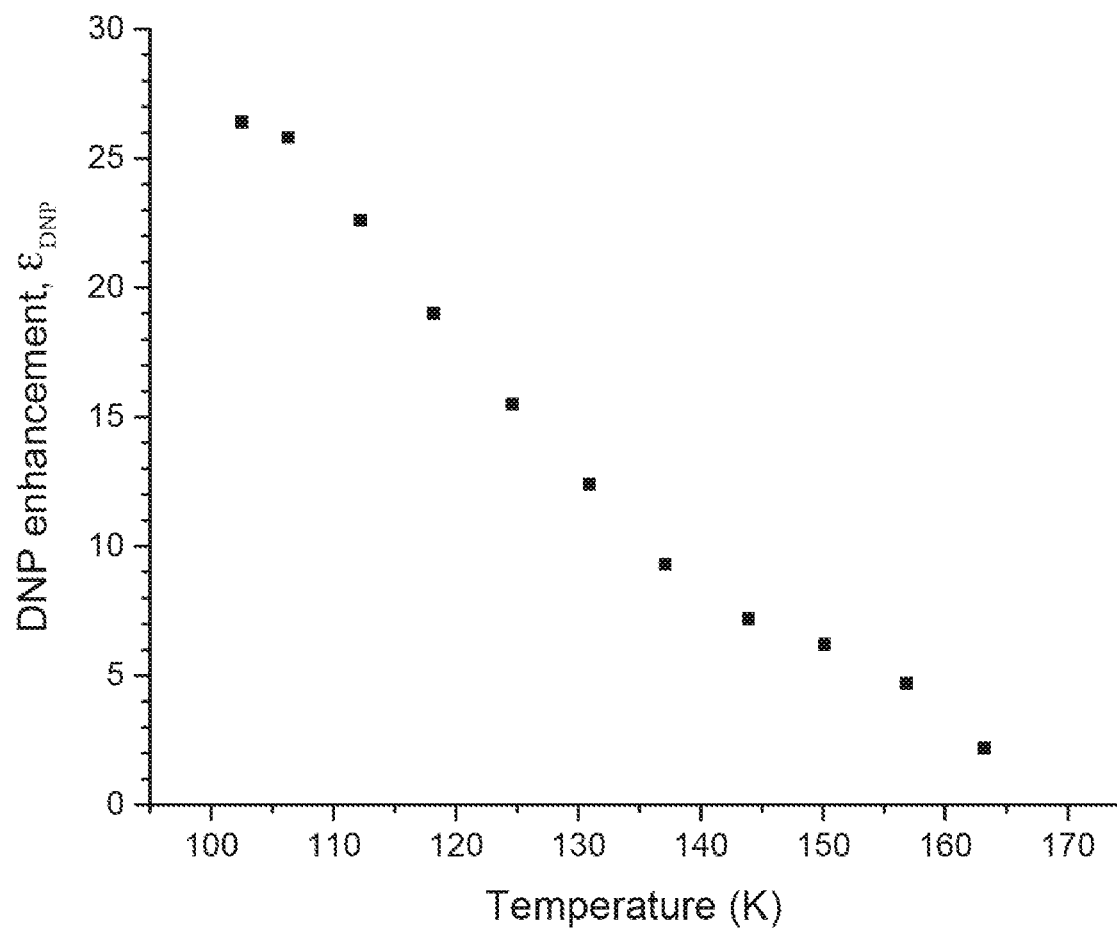
FIG. 11B shows DNP enhancements as a function of temperature, with microwave-on spectra are compared to microwave-off spectra of approximately the same temperature.

FIG. 11A shows DNP enhancements as a function of magic angle spinning (MAS) frequency from 5 kHz to 12 kHz, where microwave-on spectra are compared to microwave-off spectra at the same spinning speed. FIG. 11B show's DNP enhancements as a function of temperature, with microwave-on spectra are compared to microwave-off spectra of approximately the same temperature.

Figure 12:
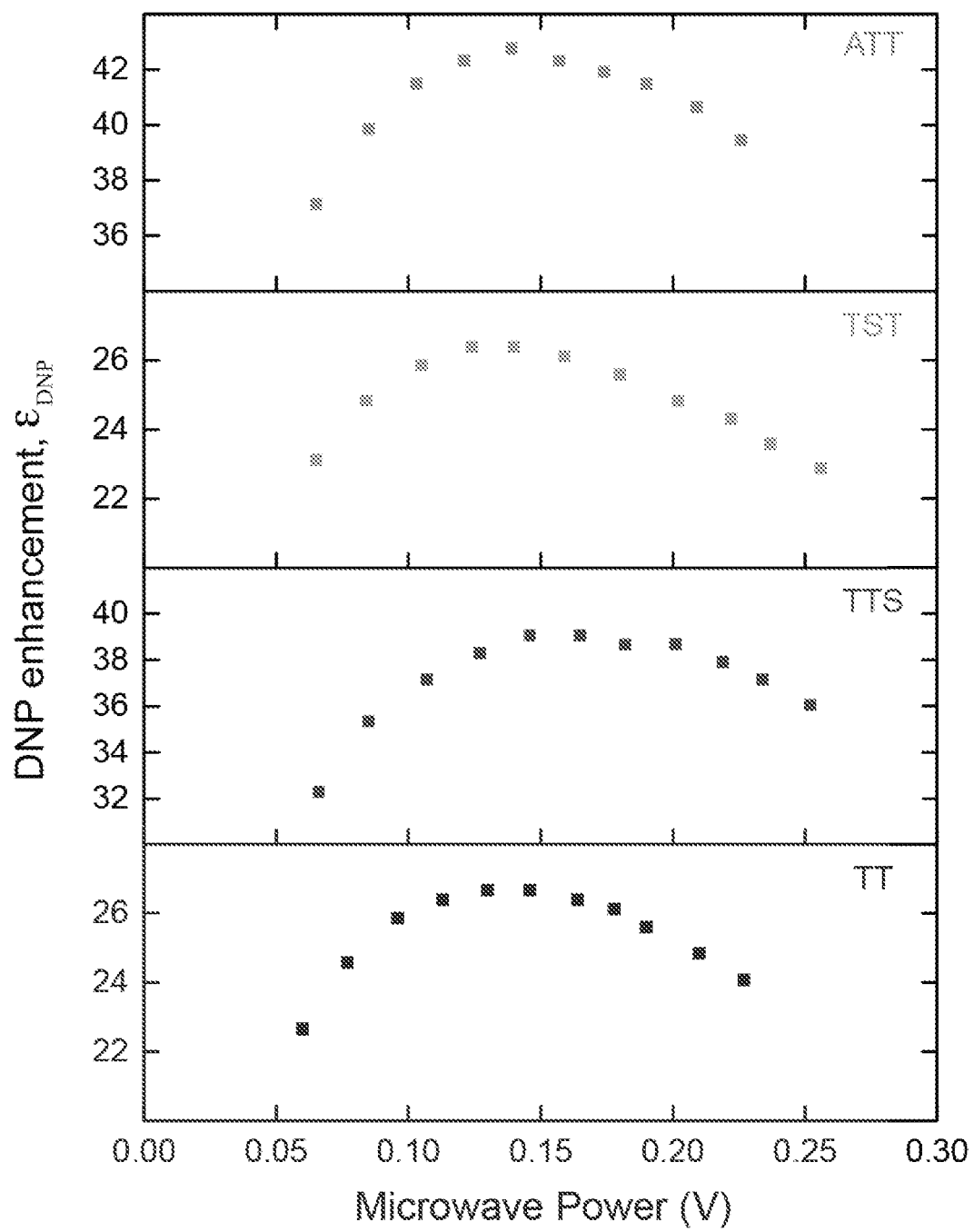
FIG. 12 shows microwave power curves for TOAC-TOAC (TT), TOAC-TOAC-Ser (TTS), TOAC-Ser-TOAC (TTS), and Acetyl-TOAC-TOAC (ATT). Microwave powers are arrayed from 0.06 V (90 mA current) to 0.25 V (140 mA current). DNP enhancements from measured from 1D 1H-13C CP experiments between microwave-on spectra and a microwave-off spectrum.

FIG. 12 show's microwave power curves for TOAC-TOAC (TT), TOAC-TOAC-Ser (TTS), TOAC-Ser-TOAC (TTS), and Acetyl-TOAC-TOAC (ATT). Microwave powers are arrayed from 0.06 V (90 mA current) to 0.25 V (140 mA current). DNP enhancements from measured from 1D 1H-13C CP experiments between microwave-on spectra and a microwave-off spectrum.

Figure 13:
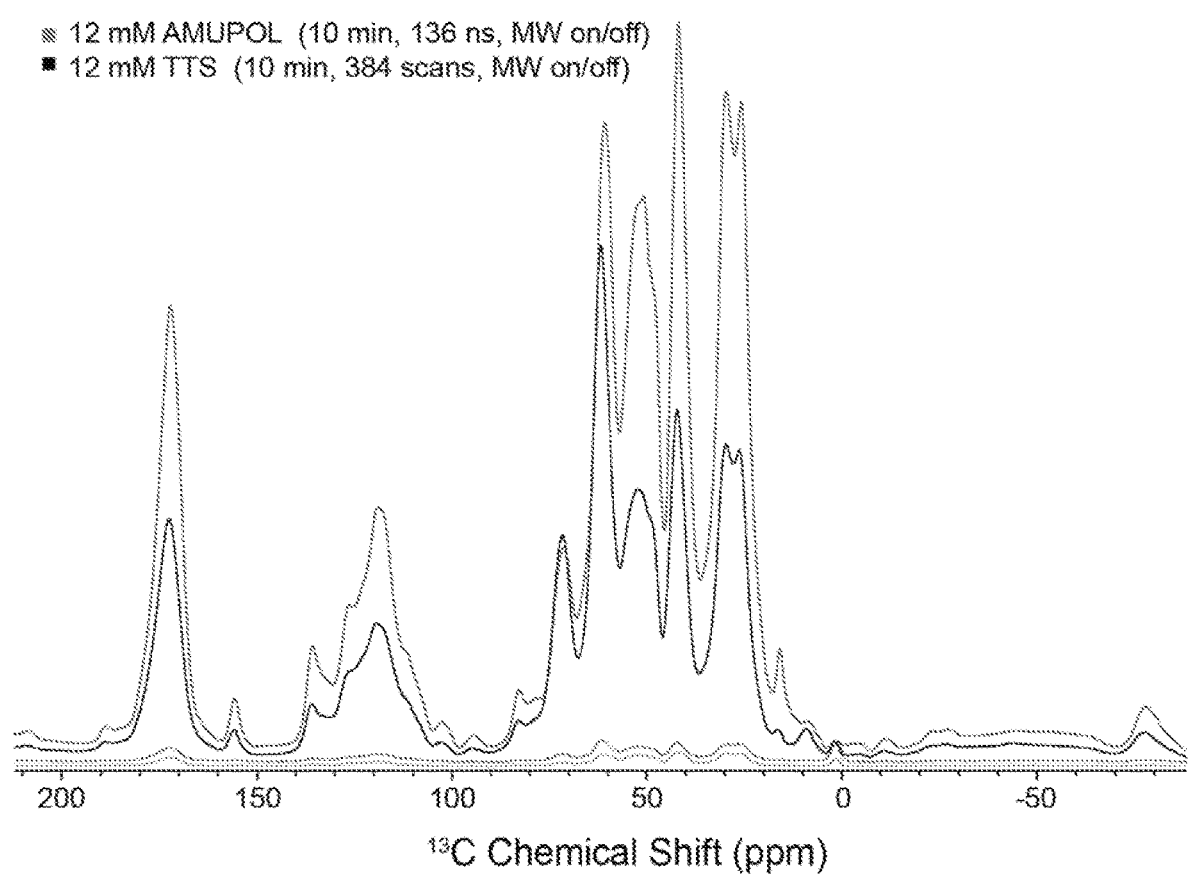
FIG. 13 shows a 1D $^1$H-$^{13}$C CP experiment of $^{13}$C,$^{15}$N-wt-huPrP23-144 fibrils prepared with 12 mM AMUPOL and 12 mM TTS in 6:3:1 d8-glycerol/D$_2$O/H$_2$O (v/v/v). Both DNP enhanced (microwave on) spectra and microwave off spectra are shown using optimal recycle delays. The number of scans was adjusted to achieve a 10-minute experiment.

The DNP-SSNMR of $^{13}$C,$^{15}$N-wt-huPrP23-144 fibrils with both AMUPOL and TTS. The DNP properties of $^{13}$C,$^{15}$N-wt-huPrP23-144 fibril samples containing 12 mM AMUPOL and 12 mM TTS in 6:3:1 d$^8$-glycerol/D$_2$O/H$_2$O (v/v/v) are included in Table 3 below. FIG. 13 shows a 1D CP experiment of $^{13}$C,$^{15}$N-wt-huPrP23-144 fibrils prepared with 12 mM AMUPOL and 12 mM TTS in 6:3:1 d8-glycerol/D$_2$O/H$_2$O (v/v/v). Both DNP enhanced (microwave on) spectra and microwave off spectra are shown using optimal recycle delays. The number of scans was adjusted to achieve a 10-minute experiment.

TABLE 3

DNP properties of $^{13}$C, $^{15}$N-wt-huPrP23-144 fibril samples containing 12 mM AMUPOL and 12 mM TTS in 6:3:1 d$^8$-glycerol/D$_2$O/H$_2$O (v/v/v).

| | 12 mM AMUPOL | 12 mM TTS |
|---|---|---|
| εDNP | 51 | 18-25 |
| τDNP (s) | 3.30 | 1.21 |

TABLE 3-continued

| DNP properties of $^{13}C$, $^{15}N$-wt-huPrP23-144 fibril samples containing 12 mM AMUPOL and 12 mM TTS in 6:3:1 $d^8$-glycerol/$D_2O$/$H_2O$ (v/v/v). | | |
|---|---|---|
| | 12 mM AMUPOL | 12 mM TTS |
| $^1H$ $T_1$ (s) | 3.35 | 1.29 |
| Optimal recycle delay (s) | 4.15 | 1.52 |

The compounds and methods of the appended claims are not limited in scope by the specific compounds and methods described herein, which are intended as illustrations of a few aspects of the claims. Any compounds and methods that are functionally equivalent are intended to fail within the scope of the claims. Various modifications of the compounds and methods in addition to those shown and described herein are intended to fall within the scope of the appended claims. Further, while only certain representative compounds and method steps disclosed herein are specifically described, other combinations of the compounds and method steps also are intended to fail within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A compound defined by Formula I

Formula I 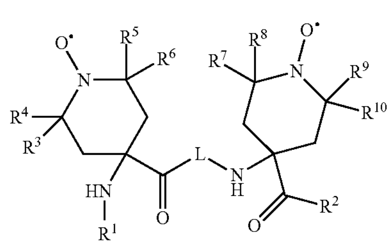 wherein

L represents a direct bond or one amino acid residue;

$R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl) carbamyl, amino acid, poly(amino acid), and poly (alkylene oxide), each optionally substituted with 1, 2, 3, or 4 independently selected $R^X$ groups;

$R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups;

$R^3$ and $R^4$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^3$ and $R^4$, together with the carbon atom to which they are attached, form a 3-10 membered cycloalkyl or 4-10 membered heterocycloalkyl ring each optionally substituted with 1, 2, 3, or 4 independently selected $R^X$ groups;

$R^5$ and $R^6$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^5$ and $R^6$, together with the carbon atom to which they are attached, form a 3-10 membered cycloalkyl or 4-10 membered heterocycloalkyl ring each optionally substituted with 1, 2, 3, or 4 independently selected $R^X$ groups;

$R^7$ and $R^8$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^7$ and $R^8$, together with the carbon atom to which they are attached, form a 3-10 membered cycloalkyl or 4-10 membered heterocycloalkyl ring each optionally substituted with 1, 2, 3, or 4 independently selected $R^X$ groups;

$R^9$ and $R^{10}$ are independently selected from group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, each optionally substituted with 1, 2, 3, or 4 independently selected $R^X$ groups; or $R^9$ and $R^{10}$, together with the carbon atom to which they are attached, form a 3-10 membered cycloalkyl or 4-10 membered heterocycloalkyl ring each optionally substituted with 1, 2, 3, or 4 independently selected $R^X$ groups;

$R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO-$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

wherein when $R^1$ and $R^2$ are poly(amino acid), the poly(amino acid) group comprises from 2 to 4 amino acid residues;

wherein when L is a direct bond, $R^1$ is not hydrogen and $R^2$ is not hydroxy; and wherein when one or more of L, $R^1$, and $R^2$ comprise an amino acid residue, at least one of these amino acid residues is not alanine.

2. The compound of claim 1, wherein the compound is defined by Formula IA

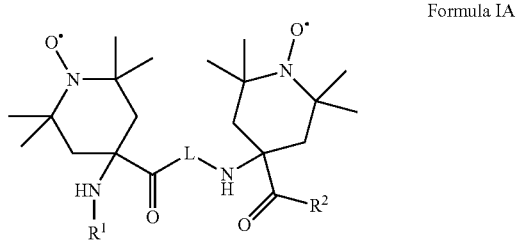

Formula IA wherein

L represents a direct bond or one amino acid residue;

$R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups;

$R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups;

$R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO-$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

wherein when $R^1$ and $R^2$ are poly(amino acid), the poly(amino acid) group comprises from 2 to 4 amino acid residues;

wherein when L is a direct bond, $R^1$ is not hydrogen and $R^2$ is not hydroxy; and wherein when one or more of L, $R^1$, and $R^2$ comprise an amino acid residue, at least one of these amino acid residues is not alanine.

3. The compound of claim 1, wherein the compound is defined by Formula IB

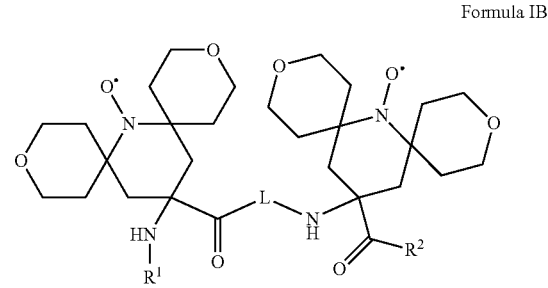

Formula IB wherein

L represents a direct bond or one amino acid residue;

$R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly (alkylene oxide), each optionally substituted with 1, 2, 3, or 4 independently selected $R^X$ groups;

$R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups;

$R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

4. The compound of claim 1, wherein the compound is defined by Formula IC

Formula IC

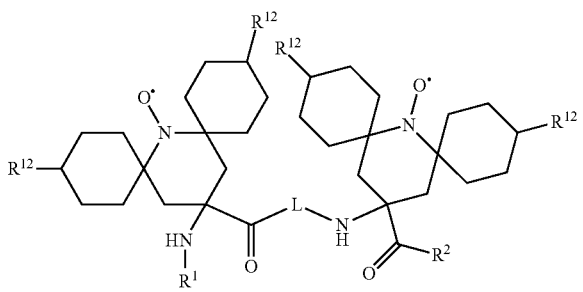

wherein

L represents a direct bond or one amino acid residue;

$R^1$ is selected from the group consisting of hydrogen, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $C_{1-12}$ alkylcarbonyl, $C_{1-12}$ alkoxycarbonyl, $C_{1-12}$ alkylcarbamyl, di($C_{1-12}$-alkyl)carbamyl, amino acid, poly(amino acid), and poly(alkylene oxide), each optionally substituted with 1, 2, 3, or 4 independently selected $R^X$ groups;

$R^2$ is selected from the group consisting of hydrogen, hydroxy, —$OR^{11}$, $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, amino, $C_{1-12}$ alkylamino; di($C_{1-12}$-alkyl)amino, amino acid, poly(amino acid), and poly(alkylene oxide), each optionally substituted with 1, 2, 3, or 4 independently selected $R^X$ groups;

$R^{11}$ is selected from the group consisting of $C_{1-6}$ alkyl, $C_{2-6}$ alkenyl, $C_{2-6}$ alkynyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide), each optionally substituted with 1, 2, 3, or 4 independently selected $R^X$ groups;

$R^{12}$ is selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, and poly(alkylene oxide); and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

5. The compound of claim 1, wherein L represents a direct bond.

6. The compound of claim 1, wherein L comprises one amino acid residue.

7. The compound of claim 6, wherein L is defined by the structure below

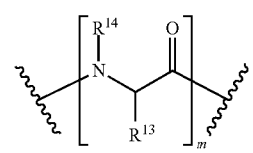

wherein for each occurrence in L, $R^{14}$ is H and $R^{13}$ is selected from one of the following

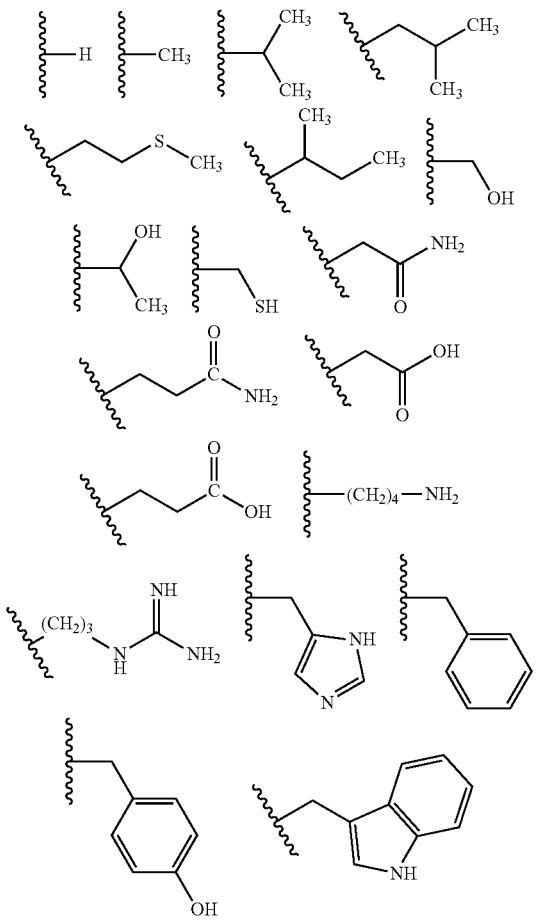

or $R^{13}$ and $R^{14}$, together with the atoms to which they are attached, form a five-membered heterocycle defined by the structure below

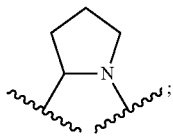 [SMILES: *C1CCCN1*]

m is 1.

8. The compound of claim 6, wherein L comprises a serine residue or a threonine residue.

9. The compound of claim 6, wherein L comprises a 2,2,6,6-tetramethyl-N-oxyl-4-amino-4-carboxylic acid residue.

10. The compound of claim 6, wherein L comprises an asparagine residue.

11. The compound of claim 6, wherein L comprises a glutamine residue.

12. The compound of claim 6, wherein L comprises an aspartic acid residue or a glutamic acid residue.

13. The compound of claim 6, wherein L comprises a cysteine residue.

14. The compound of claim 1, wherein L comprises from 3 to 20 atoms.

15. The compound of claim 1, wherein $R^1$ is H.

16. The compound of claim 1, wherein $R^1$ comprises an amino acid residue.

17. The compound of claim 16, wherein the amino acid residue is selected from the group consisting of a serine residue, a threonine residue, an asparagine residue, a glutamine residue, an aspartic acid residue, a cysteine residue, a 2,2,6,6-tetramethyl-N-oxyl-4-amino-4-carboxylic acid residue, and a glutamic acid residue.

18. The compound of claim 1, wherein $R^1$ comprises an acetyl group.

19. The compound of claim 1, wherein $R^2$ comprises a hydroxy group.

20. The compound of claim 1, wherein $R^2$ comprises an amino acid residue.

21. The compound of claim 20, wherein the amino acid residue is selected from the group consisting of a serine residue, a threonine residue, an asparagine residue, a glutamine residue, an aspartic acid residue, a cysteine residue, a 2,2,6,6-tetramethyl-N-oxyl-4-amino-4-carboxylic acid residue, and a glutamic acid residue.

22. The compound of claim 1, wherein the compound is

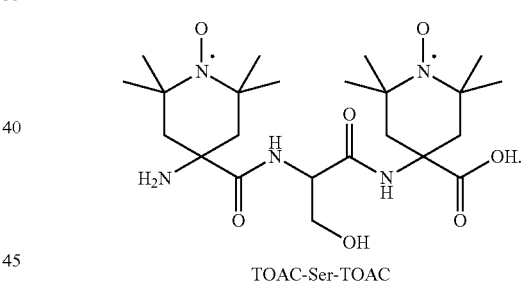

TOAC-Ser-TOAC

23. The compound of claim 1, wherein when one or more of L, $R^1$, ad $R^2$ comprise an amino acid residue selected from the group consisting of a serine residue, a threonine residue, an asparagine residue, a glutamine residue, an aspartic acid residue, a cysteine residue, a 2,2,6,6-tetramethyl-N-oxyl-4-amino-4-carboxylic acid residue, and a glutamic acid residue.

* * * * *